(12) United States Patent
Benn

(10) Patent No.: US 8,920,521 B1
(45) Date of Patent: *Dec. 30, 2014

(54) AGENT FOR ALTERING THE COLOR OF KERATIN FIBERS COMPRISING A RHEOLOGY MODIFYING POLYMER AND HIGH LEVELS OF A FATTY SUBSTANCE IN A CREAM SYSTEM

(71) Applicant: L'Oreal, Paris (FR)

(72) Inventor: Mark Benn, Union, NJ (US)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/042,835

(22) Filed: Oct. 1, 2013

(51) Int. Cl.
*A61Q 5/10* (2006.01)
*A61K 8/04* (2006.01)

(52) U.S. Cl.
CPC .. *A61K 8/042* (2013.01); *A61Q 5/10* (2013.01)
USPC ................. 8/405; 8/406; 8/552; 8/558; 8/111

(58) Field of Classification Search
USPC ..................... 8/405, 406, 552, 558, 580, 111
See application file for complete search history.

(56) References Cited

U.S. PATENT DOCUMENTS

| | | | |
|---|---|---|---|
| 5,560,750 A * | 10/1996 | Crews et al. ....................... 8/431 |
| 6,635,702 B1 | 10/2003 | Schmucker-Castner et al. |
| 6,897,253 B2 | 5/2005 | Schmucker-Castner et al. |
| 7,217,752 B2 | 5/2007 | Schmucker-Castner et al. |
| 7,494,513 B2 | 2/2009 | Kravtchenko et al. |
| 7,531,497 B2 | 5/2009 | Midha et al. |
| 7,651,534 B2 | 1/2010 | Kravtchenko et al. |
| 7,651,991 B2 | 1/2010 | Kohut et al. |
| 7,776,104 B2 | 8/2010 | Kravtchenko et al. |
| 7,879,113 B2 | 2/2011 | Simonet et al. |
| 7,901,464 B2 | 3/2011 | Hercouet et al. |
| 7,905,925 B2 | 3/2011 | Kravtchenko et al. |
| 7,905,927 B2 | 3/2011 | Hercouet |
| 7,909,887 B2 | 3/2011 | Hercouet |
| 7,909,888 B2 | 3/2011 | Hercouet et al. |
| 7,914,591 B2 | 3/2011 | Hercouet et al. |
| 7,918,902 B2 | 4/2011 | Hercouet et al. |
| 7,918,903 B2 | 4/2011 | Audousset et al. |
| 7,922,777 B2 | 4/2011 | Hercouet et al. |
| 7,927,380 B2 | 4/2011 | Audousset et al. |
| 7,927,381 B2 | 4/2011 | Hercouet |
| 7,927,382 B2 | 4/2011 | Audousset et al. |
| 7,927,383 B2 | 4/2011 | Hercouet et al. |
| 7,931,698 B2 | 4/2011 | Simonet et al. |
| 7,935,154 B2 | 5/2011 | Hercouet et al. |
| 7,947,089 B2 | 5/2011 | Hercouet et al. |
| 7,981,165 B2 | 7/2011 | Simonet et al. |
| 7,988,737 B2 | 8/2011 | Hercouet et al. |
| 7,988,738 B2 | 8/2011 | Hercouet et al. |
| 8,066,781 B2 | 11/2011 | Hercouet et al. |
| 8,070,831 B2 | 12/2011 | Simonet et al. |
| 8,092,553 B2 | 1/2012 | Giafferi et al. |
| 8,105,569 B2 | 1/2012 | Burgo |
| 8,110,533 B1 | 2/2012 | Tsaur |
| 8,118,884 B2 | 2/2012 | Ascione et al. |
| 8,142,518 B2 | 3/2012 | Deconinck et al. |
| 8,147,564 B2 | 4/2012 | Deconinck et al. |
| 8,187,338 B2 | 5/2012 | Lane et al. |
| 8,262,739 B2 | 9/2012 | Hercouet et al. |
| 8,721,739 B2 * | 5/2014 | Benn ................................. 8/405 |
| 8,721,740 B2 * | 5/2014 | Benn ................................. 8/405 |
| 8,721,741 B2 * | 5/2014 | Benn ................................. 8/405 |
| 8,721,742 B2 * | 5/2014 | Benn ................................. 8/405 |
| 2005/0071931 A1 | 4/2005 | Yoshida et al. |
| 2005/0201965 A1 | 9/2005 | Kuhlman et al. |
| 2007/0006397 A1 | 1/2007 | Schmenger et al. |
| 2007/0161524 A1 | 7/2007 | Counradi et al. |
| 2007/0213243 A1 | 9/2007 | Yao et al. |
| 2008/0031842 A1 | 2/2008 | Kuhlman et al. |
| 2008/0201870 A1 | 8/2008 | Vena et al. |
| 2009/0162309 A1 | 6/2009 | Hercouet et al. |
| 2009/0196841 A1 | 8/2009 | Song et al. |
| 2009/0202598 A1 | 8/2009 | Kravtchenko et al. |
| 2009/0300858 A1 | 12/2009 | Jo et al. |
| 2010/0035783 A1 | 2/2010 | Restrepo et al. |
| 2010/0158839 A1 | 6/2010 | Braida-Valerio et al. |
| 2010/0158844 A1 | 6/2010 | Braida-Valerio et al. |
| 2010/0166688 A1 | 7/2010 | Hercouet et al. |
| 2010/0186764 A1 | 7/2010 | Pasquet et al. |
| 2011/0155166 A1 | 6/2011 | Deconinck et al. |
| 2011/0180449 A1 | 7/2011 | Rubin |
| 2011/0195035 A1 | 8/2011 | Vondruska et al. |
| 2012/0093748 A1 | 4/2012 | Fares et al. |
| 2012/0317734 A1 | 12/2012 | Martinez-Santiago et al. |
| 2013/0081647 A1 | 4/2013 | Vohra et al. |
| 2013/0210696 A1 | 8/2013 | Vethamuthu et al. |

FOREIGN PATENT DOCUMENTS

| | | |
|---|---|---|
| EP | 0882444 A2 | 12/1998 |
| EP | 0970685 A1 | 1/2000 |
| EP | 2301521 A2 | 3/2011 |
| FR | 2852823 A1 | 10/2004 |
| JP | 2004010556 A | 1/2004 |
| JP | 2004315377 A | 11/2004 |

(Continued)

OTHER PUBLICATIONS

U.S. Appl. No. 14/042,823, filed Oct. 1, 2013, Mark Benn.

*Primary Examiner* — Eisa Elhilo
(74) *Attorney, Agent, or Firm* — L'Oreal USA

(57) ABSTRACT

The present invention is drawn to an agent and process for altering the color of keratin fibers wherein the agent comprises: (A) a color base composition containing from about 50% to about 80% by weight of a fatty substance comprising a viscosity greater than about 50 $mm^2$/s at 40° C.; and optionally, an additional fatty substance; a rheology modifying polymer; an alkalizing agent; a short alkyl chain hydroxy compound chosen from monoalcohols and polyols; an oxidative dye precursor; and an oxidizing composition comprising an oxidizing agent; and wherein the pH of the agent for altering the color of keratin fibers ranges from about 1 to about 7.

41 Claims, No Drawings

(56) References Cited

FOREIGN PATENT DOCUMENTS

| | | |
|---|---|---|
| JP | 2007320895 A | 12/2007 |
| JP | 2008063312 A | 3/2008 |
| WO | 2010/133575 A2 | 11/2010 |
| WO | 2011/116844 A2 | 9/2011 |
| WO | 2011116993 A2 | 9/2011 |
| WO | 2012/089688 A2 | 7/2012 |
| WO | 2012/150098 A2 | 11/2012 |
| WO | 2012150098 A2 | 11/2012 |
| WO | EP2013/070472 | 10/2013 |
| WO | EP2013/070473 | 10/2013 |
| ZA | 9904142 A | 12/1999 |

\* cited by examiner

AGENT FOR ALTERING THE COLOR OF KERATIN FIBERS COMPRISING A RHEOLOGY MODIFYING POLYMER AND HIGH LEVELS OF A FATTY SUBSTANCE IN A CREAM SYSTEM

FIELD OF THE INVENTION

The present invention relates to an agent for altering the color of keratinous substrates, including human keratin fibers such as the hair. The agent for altering the color of keratin fibers is provided in the form of an alkaline cream emulsion and comprises a color base composition containing a rheology modifying polymer and high levels of a fatty substance and an oxidizing composition containing an oxidizing agent.

BACKGROUND OF THE INVENTION

It is known that consumers desire to use cosmetic and personal care compositions that enhance the appearance of keratin fibers such as hair by changing the color of the hair and/or by imparting various properties to hair such as shine and conditioning. The process of changing the color of hair can involve either depositing an artificial color onto the hair which provides a different shade or color to the hair or lifting the color of the hair, such as for example, from a dark brown shade to a medium brown or a light brown shade.

Conventional hair coloring products include permanent hair dyeing products, also known as oxidation dyeing, which use the combination of compositions containing oxidative dye precursors, also known as primary intermediates or oxidation bases, and oxidizing products containing oxidizing agents such as peroxide and persulfate compounds, under alkaline pH conditions in the vast majority of cases. In general, the oxidation dye precursors comprise oxidation bases chosen from ortho- or para-phenylenediamines, ortho- or para-aminophenols, and heterocyclic compounds. These oxidation bases are colorless or weakly colored compounds, which, when combined with oxidizing products, can give access to colored species via a process of oxidative condensation.

The shades obtained with these oxidation bases may often be varied by combining them with at least one coupler, these couplers being chosen, for example, from aromatic meta-diamines, meta-aminophenols, meta-diphenols, and certain heterocyclic compounds, such as indole compounds. The variety of molecules used as oxidation bases and couplers can allow a wide range of colors to be obtained.

The oxidizing agent employed in permanent dyeing compositions may degrade the melanin of the hair, which, depending on the nature of the oxidizing agent present, may lead to less pronounced lightening of the fibers. Thus, for relatively weak lightening, the at least one oxidizing agent may be, for example, hydrogen peroxide. When more substantial lightening is desired, peroxygenated salts, such as persulfates, may be used in the presence of hydrogen peroxide.

Hair coloring compositions typically contain an alkalizing agent such as aqueous ammonia, not only for activating the oxidizing agent but also to cause the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair. However, the use of alkalizing agents, particularly, ammonia may affect the user, not only because of the undesirable odor of ammonia, but because alkalizing agents may also pose greater risks of intolerance, for instance, irritation of the scalp and stinging and may cause more degradation of the hair fibers.

The option of oxidatively dyeing hair in an acidic medium wherein all or part of the alkalizing agent is replaced by an acidifying agent has been explored. However, acidic dyeing systems may not be as efficient as alkalizing dyeing systems with respect to the degree of color deposit and intensity of color provided and with coloration time.

Thus, there is a need in the art for improved and/or alternate dyeing processes performed in the presence of at least one oxidizing agent, which do not have at least one of the drawbacks of the existing processes.

Thus, in order to improve the performance of such hair coloring compositions, the use of new and additional ingredients and novel combinations of ingredients are continuously sought; however, the choice of ingredients could pose difficulties insofar as they must improve the dyeing/lifting capability of the composition without being detrimental to other properties of the composition such as its application, rheology or viscosity properties, stability and/or resulting into more disadvantages such as increased damage or a less healthy look to the hair.

It is also important to provide hair coloring compositions with various types of consistency, such that the compositions can be provided in the form of a liquid emulsion, such as a liquid-lotion, liquid-gel, liquid-cream, or a cream emulsion, such as a thick cream or gel-cream, or a foam or mousse wherein the liquid emulsion form has a thinner consistency than the cream emulsion form and is typically packaged in a bottle. The liquid emulsion form is generally employed when the entire head of hair is to be colored or when only one color is desired since the dye composition spreads easily, allowing for greater coverage while the cream emulsion form can be employed for dyeing the entire head of hair and for highlighting or lightening only certain sections of the hair.

Thus, the objective of the present invention is to obtain novel compositions for oxidatively dyeing the hair. Another objective of the invention is to obtain hair coloring compositions that have a unique, non-drip consistency or rheology and yet spreads easily on the hair while imparting other advantages to the hair such as conditioning, a healthy appearance, shine and less damage to the hair.

BRIEF SUMMARY OF THE INVENTION

In order to achieve these and other advantages, the present invention is drawn to an agent for altering the color of keratin fibers comprising:

(A) a color base composition, containing, in a cosmetically acceptable medium:
  (a) from about 50% to about 80% by weight of a fatty substance or a mixture of fatty substances comprising:
    (i) at least 5% by weight of at least one fatty substance having a viscosity greater than about 50 mm$^2$/s at 40° C.; and
    (ii) from 0% to about 75% by weight of at least one additional fatty substance other than (A)(a)(i);
  all weights being based on the total weight of (A);
  (b) at least one rheology modifying polymer selected from a crosslinked acrylate polymer in aqueous dispersion;
  (c) at least one alkalizing agent;
  (d) at least one short alkyl chain hydroxy compound chosen from monoalcohols and polyols;
  (e) at least one oxidative dye precursor; and (B) an oxidizing composition comprising, in a cosmetically acceptable medium, at least one oxidizing agent; and wherein the pH of the agent for altering the color of keratin fibers ranges from about 1 to about 7.

The present invention is also drawn to a process of coloring keratinous fibers, comprising applying onto the keratin fibers the above-disclosed agent for altering the color of keratin fibers, such as hair, wherein the color base and oxidizing compositions are mixed to form said agent before applying it onto the fibers; and leaving said agent on the keratin fibers for a period of time sufficient to color the fibers.

DETAILED DESCRIPTION OF THE INVENTION

Other than in the operating examples, or where otherwise indicated, all numbers expressing quantities of ingredients and/or reaction conditions are to be understood as being modified in all instances by the term "about" which encompasses±10%.

"At least one" as used herein means one or more and thus includes individual components as well as mixtures/combinations.

"Keratinous fiber" may be chosen from, for example, human hair.

"Formed from," as used herein, means obtained from chemical reaction of, wherein "chemical reaction," includes spontaneous chemical reactions and induced chemical reactions. As used herein, the phrase "formed from", is open ended and does not limit the components of the composition to those listed, e.g., as component (i) and component (ii). Furthermore, the phrase "formed from" does not limit the order of adding components to the composition or require that the listed components (e.g., components (i) and (ii)) be added to the composition before any other components.

"Hydrocarbons," as used herein, include alkanes, alkenes, and alkynes, wherein the alkanes comprise at least one carbon, and the alkenes and alkynes each comprise at least two carbons; further wherein the hydrocarbons may be chosen from linear hydrocarbons, branched hydrocarbons, and cyclic hydrocarbons; further wherein the hydrocarbons may optionally be substituted; and further wherein the hydrocarbons may optionally further comprise at least one heteroatom intercalated in the hydrocarbon chain.

"Silicone compound," as used herein, includes, for example, silica, silanes, silazanes, siloxanes, and organosiloxanes; and refers to a compound comprising at least one silicon; wherein the silicone compound may be chosen from linear silicone compounds, branched silicone compounds, and cyclic silicone compounds; further wherein the silicone compound may optionally be substituted; and further wherein the silicone compound may optionally further comprise at least one heteroatom intercalated in the silicone chain, wherein the at least one heteroatom is different from the at least one silicon.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Polymers," as defined herein, include homopolymers and copolymers formed from at least two different types of monomers.

The term "substantially free of ammonia" as defined herein means that the compositions or agent for altering the color of keratin fibers of the present invention is either completely free of ammonia (including ammonium ions) or contains no appreciable amount of ammonia (including ammonium ions), for example, no more than 1% by weight, or no more than 0.5% by weight, or no more than 0.3% by weight, or no more than 0.1% by weight, based on the weight of the compositions or agent for altering the color of keratinous substrates.

It has been surprisingly and unexpectedly discovered that when the color base and oxidizing compositions were mixed, the resulting agent for altering the color of keratin fibers (also called ready-to-use composition) had improved dyeing properties. For example, the agent for altering the color of keratin fibers provided coloring with good strength and/or intensity and/or good uniformity of the color along the fiber between the tip and the root of the hair (also called the selectivity of coloring) and/or good chromaticity. In addition, the agent for altering the color of keratin fibers can be applied without difficulty onto keratin fibers without running or dripping.

It has also been surprisingly and unexpectedly found that the color of hair can be effectively altered according to the present disclosure at a lowered cost and less time of production because lower amounts of dye compounds can be employed and the color base composition of the present invention can be prepared without the use of heat or using a cold process method.

Fatty Substances

The color base composition or the color base composition of the present invention comprises at least one fatty substance having a viscosity of greater than about 50 mm$^2$/s at 40° C.

The viscosity of the at least one fatty substance having a viscosity of greater than about 50 mm$^2$/s at 40° C. of the present invention is measured as kinematic viscosity according to the ASTM D445 method and may range from between greater than about 50 to about 100 mm$^2$/s at 40° C., preferably from about 50 to about 100 mm$^2$/s at 40° C.

The at least one fatty substance having a viscosity of greater than about 50 mm$^2$/s at 40° C. may be chosen from oils such as mineral oil (kinematic viscosity as measured by the ASTM D 445 method in units of mm$^2$/s at 40° C.)

A preferred fatty substance having a viscosity of greater than 50 mm$^2$/s at 40° C. is a mineral oil having a viscosity ranging from between about 63 to about 70 mm$^2$/s at 40° C., commercially available from the supplier Sonneborn under the tradename Kaydol® Heavy White Mineral Oil or from the supplier Exxonmobil Chemical under the tradename Primol™ 352.

The at least one fatty substance having a viscosity of greater than about 50 mm$^2$/s at 40° C. may also be referred to hereinafter as "high viscosity mineral oil."

The color base composition of the present invention may further comprise an additional fatty substance other than the fatty substance having a viscosity of greater than about 50 mm$^2$/s at 40° C.

"Fatty substance" means an organic compound insoluble in water at normal temperature (25° C.) and at atmospheric pressure (750 mmHg) (solubility below 5% and such as below 1% and further such as below 0.1%). Fatty substances have in their structure a chain of at least two siloxane groups or at least one hydrocarbon chain having at least 6 carbon atoms. Moreover, fatty substances are generally soluble in organic solvents in the same conditions of temperature and pressure, for example in chloroform, ethanol, benzene or decamethylcyclopentasiloxane.

Fatty substances are, for example, chosen from lower alkanes, fatty alcohols, esters of fatty acid, esters of fatty alcohol, fatty acids, oils such as mineral, vegetable, animal and synthetic non-silicone oils, non-silicone waxes and silicones.

In some embodiments, the alcohols and esters have at least one linear or branched, saturated or unsaturated hydrocarbon group, comprising 6 to 30 carbon atoms, optionally substituted, for example, with at least one hydroxyl group (for example 1 to 4). If they are unsaturated, these compounds can have one to three, conjugated or unconjugated, carbon-carbon double bonds.

With regard to the lower alkanes, in some embodiments, these have from 6 to 16 carbon atoms and are linear or branched, optionally cyclic. As examples, alkanes can be chosen from hexane and dodecane, isoparaffins such as isohexadecane and isodecane.

Non-limiting examples of non-silicone oils usable in the composition of the disclosure, include: hydrocarbon oils of animal origin, such as perhydrosqualene; hydrocarbon oils of vegetable origin, such as liquid triglycerides of fatty acids having from 6 to 30 carbon atoms such as triglycerides of heptanoic or octanoic acids, or for example sunflower oil, maize oil, soya oil, cucurbit oil, grapeseed oil, sesame oil, hazelnut oil, apricot oil, macadamia oil, arara oil, sunflower oil, castor oil, avocado oil, triglycerides of caprylic/capric acids such as those sold by the company Stearineries Dubois or those sold under the names MIGLYOL® 810, 812 and 818 by the company Dynamit Nobel, jojoba oil, shea butter oil; hydrocarbons with more than 16 carbon atoms, linear or branched, of mineral or synthetic origin, such as paraffin oils, petroleum jelly, liquid paraffin, polydecenes, hydrogenated polyisobutene such as Parleam®. fluorinated, partially hydrocarbon oils; as fluorinated oils, non-limiting examples include perfluoromethylcyclopentane and perfluoro-1,3-dimethylcyclohexane, sold under the names "FLUTEC® PC1" and "FLUTEC® PC3" by the company BNFL Fluorochemicals; perfluoro-1,2-dimethylcyclobutane; perfluoroalkanes such as dodecafluoropentane and tetradecafluorohexane, sold under the names "PF 5050®" and "PF 5060®" by the 3M Company, or bromoperfluorooctyl sold under the name "FORALKYL®" by the company Atochem; non-afluoro-methoxybutane and nonafluoroethoxyisobutane; derivatives of perfluoromorpholine, such as 4-trifluoromethyl perfluoromorpholine sold under the name "PF 5052®" by the 3M Company.

The fatty alcohols usable as fatty substances in the composition of the disclosure include, but are not limited to, non-alkoxylated, saturated or unsaturated, linear or branched, and have from 6 to 30 carbon atoms and more particularly from 8 to 30 carbon atoms; For example, cetyl alcohol, stearyl alcohol and their mixture (cetylstearyl alcohol), octyldodecanol, 2-butyloctanol, 2-hexyldecanol, 2-undecylpentadecanol, oleic alcohol or linoleic alcohol.

The exemplary non-silicone wax or waxes that can be used in the composition of the disclosure are chosen from carnauba wax, candelilla wax, and Alfa wax, paraffin wax, ozokerite, vegetable waxes such as olive wax, rice wax, hydrogenated jojoba wax or absolute waxes of flowers such as the essential wax of blackcurrant flower sold by the company BERTIN (France), animal waxes such as beeswaxes, or modified beeswaxes (cerabellina); other waxes or waxy raw materials usable according to the disclosure are, for example, marine waxes such as that sold by the company SOPHIM under reference M82, waxes of polyethylene or of polyolefins in general.

The exemplary fatty acid esters are the esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total number of carbons of the esters being, for example, greater than or equal to 10.

Among the monoesters, non-limiting mentions can be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononoate; octyl palmitate; octyl pelargonate; octyl stearate; octyldodecyl erucate; oleyl erucate; ethyl and isopropyl palmitates, ethyl-2-hexyl palmitate, 2-octyldecyl palmitate, alkyl myristates such as isopropyl, butyl, cetyl, 2-octyldodecyl, mirystyl, stearyl myristate, hexyl stearate, butyl stearate, isobutyl stearate; dioctyl malate, hexyl laurate, and 2-hexyldecyl laurate.

Further non-limiting mentions of esters can be made of the esters of $C_4$-$C_{22}$ di- or tricarboxylic acids and of $C_1$-$C_{22}$ alcohols and the esters of mono-, di- or tricarboxylic acids and of $C_2$-$C_{26}$ di-, tri-, tetra- or pentahydroxy alcohols.

Even further non-limiting examples of esters include: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisotearyl citrate; glyceryl trilactate; glyceryl trioctanoate; trioctyldodecyl citrate; trioleyl citrate, propylene glycol dioctanoate; neopentyl glycol diheptanoate; diethylene glycol diisanonate; and polyethylene glycol distearates.

Among the esters mentioned above, exemplary esters include ethyl, isopropyl, myristyl, cetyl, stearyl palmitates, ethyl-2-hexyl palmitate, 2-octyldecyl palmitate, alkyl myristates such as isopropyl, butyl, cetyl, 2-octyldodecyl myristate, hexyl stearate, butyl stearate, isobutyl stearate; dioctyl malate, hexyl laurate, 2-hexyldecyl laurate and isononyl isononanate, cetyl octanoate.

The composition can also comprise, as fatty ester, esters and di-esters of sugars of $C_6$-$C_{30}$, such as $C_{12}$-$C_{22}$ fatty acids. "Sugar" as used in the disclosure means oxygen-containing hydrocarbon compounds that possess several alcohol functions, with or without aldehyde or ketone functions, and having at least 4 carbon atoms. These sugars can be monosaccharides, oligosaccharides or polysaccharides.

As suitable sugars, non-limiting examples include sucrose, glucose, galactose, ribose, fucose, maltose, fructose, mannose, arabinose, xylose, lactose, and their derivatives, for example alkylated, such as methylated derivatives such as methylglucose.

The esters of sugars and of fatty acids can, for example, be chosen from the esters or mixtures of esters of sugars described previously and of linear or branched, saturated or unsaturated $C_6$-$C_{30}$, such as $C_{12}$-$C_{22}$ fatty acids. If they are unsaturated, these compounds can have one to three, conjugated or unconjugated, carbon-carbon double bonds.

The esters according to at least one embodiment can also be chosen from mono-, di-, tri- and tetra-esters, polyesters and mixtures thereof.

These esters can be for example oleate, laurate, palmitate, myristate, behenate, cocoate, stearate, linoleate, linolenate, caprate, arachidonates, or mixtures thereof such as the oleo-palmitate, oleo-stearate, palmito-stearate mixed esters.

For example, the mono- and di-esters can be used, and such as the mono- or di-oleate, stearate, behenate, oleopalmitate, linoleate, linolenate, oleostearate, of sucrose, of glucose or of methylglucose.

Non-limiting mention can be made of the product sold under the name GLUCATE® DO by the company Amerchol, which is a dioleate of methylglucose.

Exemplary esters or of mixtures of esters of sugar of fatty acid include: the products sold under the names F160, F140, F110, F90, F70, SL40 by the company Crodesta, denoting respectively the palmito-stearates of sucrose formed from 73% of monoester and 27% of di- and tri-ester, from 61% of monoester and 39% of di-, tri-, and tetra-ester, from 52% of monoester and 48% of di-, tri-, and tetra-ester, from 45% of monoester and 55% of di-, tri-, and tetra-ester, from 39% of monoester and 61% of di-, tri-, and tetra-ester, and the monolaurate of sucrose; the products sold under the name Ryoto Sugar Esters for example with the reference B370 and corresponding to the behenate of sucrose formed from 20% of monoester and 80% of di-triester-polyester; sucrose mono-di-palmito-stearate marketed by the company Goldschmidt under the name TEGOSOFT® PSE.

The silicones usable in the composition of the present disclosure include but are not limited to volatile or non-volatile, cyclic, linear or branched silicones, modified or not with organic groups, having a viscosity from $5 \times 10^{-6}$ to 2.5 $m^2/s$ at 25° C., such as from $1 \times 10^{-5}$ to 1 $m^2/s$.

The silicones usable according to the disclosure can be in the form of oils, waxes, resins or gums.

In some embodiments, the silicone is chosen from the polydialkylsiloxanes, such as the polydimethylsiloxanes (PDMS), and the organo-modified polysiloxanes having at least one functional group selected from the poly(alkoxy-lated) groups, the amine groups and the alkoxy groups.

The organopolysiloxanes are defined in more detail in the work of Walter NOLL "Chemistry and Technology of Silicones" (1968), Academic Press. They can be volatile or non-volatile.

When they are volatile, the silicones are, for example, chosen from those with a boiling point between 60° C. and 260° C., and for further examples, chosen from:

the cyclic polydialkylsiloxanes having from 3 to 7, such as from 4 to 5 silicon atoms. It can be, for example, the octamethylcyclotetrasiloxane marketed under the name VOLATILE SILICONE® 7207 by UNION CARBIDE or SILBIONE® 70045 V2 by RHODIA, the decamethylcyclopentasiloxane marketed under the name VOLATILE SILICONE® 7158 by UNION CARBIDE, and SILBIONE® 70045 V5 by RHODIA, and mixtures thereof.

Non-limiting mentions can also be made of the cyclocopolymers of the dimethylsiloxanes/methylalkylsiloxane type, such as SILICONE VOLATILE® FZ 3109 marketed by the company UNION CARBIDE, of the formula V:

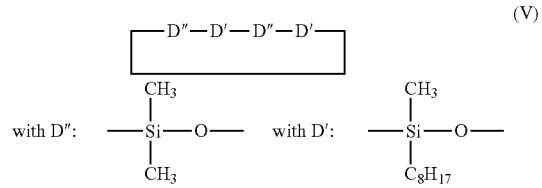

Non-limiting mentions can further be made of the mixtures of cyclic polydialkylsiloxanes with organic compounds derived from silicon, such as the mixture of octamethylcyclotetrasiloxane and tetratrimethylsilylpentaerythritol (50/50) and the mixture of octamethylcyclotetrasiloxane and oxy-1,1'-(hexa-2,2,2',2',3,3'-trimethylsilyloxy)bis-neopentane.

Other suitable volatile silicones include the linear volatile polydialkylsiloxanes having 2 to 9 silicon atoms and with a viscosity less than or equal to $5 \times 10^{-6}$ $m^2/s$ at 25° C. An example is decamethyltetrasiloxane, marketed under the name "SH 200" by the company TORAY SILICONE. Silicones included in this class are also described in the article published in Cosmetics and Toiletries, Vol. 91, January 76, p. 27-32—TODD BYERS "Volatile Silicone fluids for cosmetics".

Even further non-limiting mentions can be made of non-volatile polydialkylsiloxanes, gums and resins of polydialkylsiloxanes, polyorganosiloxanes modified with the aforementioned organofunctional groups, and mixtures thereof.

These silicones are, for example, chosen from the polydialkylsiloxanes, such as the polydimethylsiloxanes with trimethylsilyl end groups. The viscosity of the silicones is measured at 25° C. according to standard ASTM 445 Appendix C.

Among these polydialkylsiloxanes, mention can be made of, non-exhaustively, the following commercial products: the SILBIONE® oils of series 47 and 70 047 or the MIRASIL® oils marketed by RHODIA, for example the oil 70 047 V 500 000; the oils of the MIRASIL® series marketed by the company RHODIA; the oils of the 200 series from the company DOW CORNING such as DC200, with a viscosity of 60 000 $mm^2/s$; the VISCASIL® oils from GENERAL ELECTRIC and certain oils of the SF series (SF 96, SF 18) from GENERAL ELECTRIC.

Non-limiting mention can also be made of the polydimethylsiloxanes with dimethylsilanol end groups known under the name of dimethiconol (CTFA), such as the oils of the 48 series from the company RHODIA.

In this class of polydialkylsiloxanes, non-limiting mentions can be made of the products marketed under the names "ABIL WAX® 9800 and 9801" by the company GOLDSCHMIDT, which are polydialkyl ($C_1$-$C_{20}$) siloxanes.

The silicone gums usable according to the disclosure are, for example, polydialkylsiloxanes, such as polydimethylsiloxanes with high number-average molecular weights between 200,000 and 1,000,000 used alone or mixed in a solvent. This solvent can be chosen from the volatile silicones, the polydimethylsiloxane (PDMS) oils, the polyphenylmethylsiloxane (PPMS) oils, the isoparaffins, the polyisobutylenes, methylene chloride, pentane, dodecane, tridecane and mixtures thereof.

Products usable according to the disclosure are, for example, mixtures such as: mixtures formed from a chain end hydroxylated polydimethylsiloxane, or dimethiconol (CTFA) and a cyclic polydimethylsiloxane also called cyclomethicone (CTFA), such as the product Q2 1401 marketed by the company DOW CORNING; mixtures of a polydimethylsiloxane gum and a cyclic silicone such as the product SF 1214 Silicone Fluid from the company GENERAL ELECTRIC, said product being a gum SF 30 corresponding to a dimethicone, having a number-average molecular weight of 500,000, dissolved in the oil SF 1202 Silicone Fluid corresponding to decamethylcyclopentasiloxane; mixtures of two PDMS of different viscosities, for example, of a PDMS gum and a PDMS oil, such as the product SF 1236 from the company GENERAL ELECTRIC. The product SF 1236 is a mixture of a gum SE 30 as defined above having a viscosity of 20 m²/s and an oil SF 96 with a viscosity of 5×10⁻⁶ m²/s. This product, for example, has 15% of gum SE 30 and 85% of oil SF 96.

The organopolysiloxane resins usable according to the disclosure include but are not limited to crosslinked siloxane systems containing the units: $R_2SiO_{2/2}$, $R_3SiO_{1/2}$, $RSiO_{3/2}$ and $SiO_{4/2}$ in which R represents an alkyl having 1 to 16 carbon atoms. For example, R denotes a $C_1$-$C_4$ lower alkyl group such as methyl.

Among these resins, non-limiting mention can be made of the product marketed under the name "DOW CORNING 593" or those marketed under the names "SILICONE FLUID SS 4230 and SS 4267" by the company GENERAL ELECTRIC, which are silicones of dimethyl/trimethyl siloxane structure.

Non-limiting mention can also be made of the resins of the trimethylsiloxysilicate type, such as those marketed under the names X22-4914, X21-5034 and X21-5037 by the company SHIN-ETSU.

The organomodified silicones usable according to the disclosure include but are not limited to silicones as defined previously, having in their structure at least one organofunctional group fixed by a hydrocarbon group.

In addition to the silicones described above, the organomodified silicones can be polydiaryl siloxanes, such as polydiphenylsiloxanes, and polyalkyl-arylsiloxanes functionalized by the aforementioned organofunctional groups.

The polyalkarylsiloxanes are, for example, chosen from the polydimethyl/methylphenylsiloxanes, the polydimethyl/diphenylsiloxanes, linear and/or branched, with viscosity ranging from $1\times10^{-5}$ to $5\times10^2$ m²/s at 25° C.

Among these polyalkarylsiloxanes, non-limiting mentions can be made of the products marketed under the following names: the SILBIONE® oils of series 70 641 from RHODIA; the oils of the series RHODORSIL® 70 633 and 763 from RHODIA; the oil DOW CORNING 556 COSMETIC GRADE FLUID from DOW CORNING; the silicones of the PK series from BAYER such as the product PK20; the silicones of the series PN, PH from BAYER such as the products PN1000 and PH1000; certain oils of the SF series from GENERAL ELECTRIC such as SF 1023, SF 1154, SF 1250, SF 1265.

Among the organomodified silicones, non-limiting mention can be made of the polyorganosiloxanes having: polyoxyethylene and/or polyoxypropylene groups optionally with $C_6$-$C_{24}$ alkyl groups such as the products called dimethicone copolyol marketed by the company DOW CORNING under the name DC 1248 or the oils SILWET® L 722, L 7500, L 77, L 711 from the company UNION CARBIDE and the alkyl ($C_{12}$)-methicone copolyol marketed by the company DOW CORNING under the name Q2 5200; substituted or unsubstituted amine groups such as the products marketed under the name GP 4 Silicone Fluid and GP 7100 by the company GENESEE or the products marketed under the names Q2 8220 and DOW CORNING 929 or 939 by the company DOW CORNING. The substituted amine groups are, for example, $C_1$-$C_4$ aminoalkyl groups; alkoxylated groups, such as the product marketed under the name "SILICONE COPOLYMER F-755" by SWS SILICONES and ABIL WAX® 2428, 2434 and 2440 by the company GOLDSCHMIDT.

For example, the fatty substance is chosen from compounds that are liquid or pasty at room temperature and at atmospheric pressure.

For further example, the fatty substance is a compound that is liquid at a temperature of 25° C. and at atmospheric pressure.

The fatty substance is, for example, chosen from the lower alkanes, fatty alcohols, esters of fatty acid, esters of fatty alcohol, and oils such as non-silicone mineral, vegetable and synthetic oils, including silicones.

According to at least one embodiment, the fatty substance is chosen from non-silicone compounds such as liquid paraffin, polydecenes, liquid esters of fatty acids and of fatty alcohols, and mixtures thereof.

In some embodiments, the fatty substance is chosen from alkanes, hydrocarbons and silicones.

The at least one additional fatty substance of the present invention may be chosen from the above disclosed fatty substances other than the fatty substance having a viscosity of greater than about 50 mm²/s at 40° C.

In certain embodiments, the at least one additional fatty substance has a viscrosslinkedcosity of about 50 mm²/s or less at 40° C.

A preferred additional fatty substance is mineral oil having a viscosity of about 50 mm²/s or less at 40° C., for example, ranging from between about 14 to about 30 mm²/s at 40° C. and commercially available from several suppliers such as Sonneborn under the tradename Blandol, Armedsa under the tradename Aemoil M-302CG and Exxonmobil Chemical under the tradename Marcol 82.

The at least one additional fatty substance of the present invention may be employed in an amount of at least about 0.5% by weight relative to the total weight of the color base composition. For example, the amount of the at least one additional fatty substance may be from 0.5% to about 75% by weight, or such as from about 5% to about 70% by weight, or such as from about 5% to about 60% by weight, or such as from about 5% to about 50% by weight, based on the total weight of the color base composition.

The at least one fatty substance having a viscosity of greater than about 50 mm²/s at 40° C. is present in an amount of at least about 5% by weight, or from about 5% to about 80% by weight, based on the total weight of the color base composition.

In certain embodiments, the at least one fatty substance having a viscosity of greater than about 50 mm²/s at 40° C. may also be employed in an amount of from about 50% to about 80% by weight, preferably from about 50% to about 70% by weight, more preferably, from about 50% to about 60% by weight, or at about 50% by weight, or at about 60% by weight, based on the total weight of the color base composition. When the amount of the at least one fatty substance having a viscosity of greater than about 50 mm²/s at 40° C. is less than about 80% by weight, the at least one additional fatty substance may be employed in an amount such that the total amount of fatty substances is not more than about 80% by weight, based on the total weight of the color base composition.

Thus, the total amount of fatty substances, comprising the at least one fatty substance having a viscosity of greater than about 50 mm²/s at 40° C. and optionally, the at least one additional fatty substance, is at least about 50% by weight and may be employed in an amount ranging from about 50% to about 80% by weight, preferably, from about 50% to about 70% by weight, more preferably, from about 50% to about 60% by weight, based on the total weight of the color base composition.

In other embodiments, the total amount of fatty substances, comprising the at least one fatty substance having a viscosity of greater than about 50 mm²/s at 40° C. and optionally, the at least one additional fatty substance is at about 50% by weight, or at about 60% by weight, based on the total weight of the color base composition.

In preferred embodiments of the present invention, the color base composition is in the form of a cream emulsion or a liquid-cream emulsion.

In other embodiments of the present invention, the viscosity and/or amount of the at least one additional fatty substance are such that the color base composition is in the form of a cream emulsion or a liquid-cream emulsion.

In preferred embodiments, the color base composition of the present invention is in the form of a cream emulsion.

In particularly preferred embodiments of the present invention, the at least one additional fatty substance is introduced into the color base composition of the present invention after an amount of the fatty substance having a viscosity of greater than about 50 mm²/s at 40° C. has been combined with the rheology modifying polymer of the present invention.

The at least one fatty substance having a viscosity of greater than about 50 mm²/s at 40° C., the at least one additional fatty substance of the present invention and mixtures thereof may also be present in the oxidizing composition of the present invention.

Rheology Modifying Polymer

The at least one rheology modifying polymer of the present invention is selected from a crosslinked acrylate polymer in aqueous dispersion.

A preferred rheology modifying polymer of the present invention is a crosslinked copolymer of acrylic or methacrylic acid and/or one or more of their C1-C6 alkyl esters.

In certain embodiments, the crosslinked acrylate polymer in aqueous dispersion is a polymer that is selected from crosslinked (meth)acrylic acid/C1-C6 alkyl acrylate copolymers and has three structural units or is polymerized from a monomer mixture comprising three polymerizable monomeric components: one or more carboxylic acid monomers and salts thereof having 3 to 10 carbon atoms, one or more vinyl monomers, and one or more mono- or polyunsaturated monomers.

The amount of the carboxylic acid monomers is generally from about 20% to 80% by weight in one aspect, from about 25% to about 70% by weight in another aspect and from about 35% to about 65% by weight in a further aspect, based upon the total weight of the monomers.

The amount of the vinyl monomers is generally from about 80% to about 15% by weight in one aspect, from about 75% to about 25% by weight in another aspect, and from about 65% to about 35% by weight in a further aspect based upon the total weight of the monomers.

The third component, the one or more mono- or polyunsaturated monomer, is utilized to generate a partially or substantially crosslinked three-dimensional polymeric network. By polyunsaturated is meant that the crosslinking monomer contains at least two polymerizable double bonds that are reactive with the foregoing unsaturated carboxylic acid containing monomers and the vinyl monomers.

As used herein, the term "(meth)acrylic" acid and "(meth)acrylate" are meant to include the corresponding methyl derivatives of acrylic acid and the corresponding alkyl acrylate. For example, "(meth)acrylic)" acid refers to acrylic acid and/or methacrylic acid and "(meth)acrylate" refers to alkyl acrylate and/or alkyl methacrylate.

The third component can be used in an amount from about 0.01 to about 5% by weight in one aspect, from about 0.03 to about 3% by weight in another aspect, and from about 0.05 to about 1% by weight in a further aspect, based upon the total weight of all of the monomer components.

In preferred embodiments, the crosslinked acrylate polymer is slightly crosslinked.

As used herein, the term "slightly crosslinked" refers to a partially crosslinked three-dimensional polymeric network.

In other preferred embodiments, the crosslinked acrylate polymer is alkali-swellable.

As used herein, the term "alkali-swellable" as it pertains to the rheology modifying polymer of the present invention refers to a polymer that when introduced to a solution, imparts little or no viscosity, but upon adjusting the pH to mildly acidic, neutral, or mildly basic conditions, a measurable increase in viscosity is observed, i.e., adding an alkali or neutralizing agent to a solution containing an alkali swellable polymer results in the development of viscosity.

The term "alkali-swellable" as used herein may also refer to the expansion of the polymer molecules upon neutralization as a result of charge repulsion of the anionic carboxylate groups of the polymer.

A particularly preferred rheology modifying polymer of the present invention is a methacrylic acid/ethyl acrylate crosslinked copolymer.

A preferred example of the methacrylic acid/ethyl acrylate crosslinked copolymer of the present invention is a slightly crosslinked, alkali-swellable acrylate polymer known by the INCI name acrylates copolymer and commercially available from the supplier Lubrizol, under the tradename Carbopol® Aqua SF-1 as an aqueous dispersion comprising about 30% by weight of total solids. Carbopol® Aqua SF-1 has a carboxyl functionality in its protonated form. This copolymer belongs to a class of synthetic rheology modifiers that include carboxyl functional alkali-swellable and alkali-soluble thickeners (ASTs). These thickener polymers are prepared from the free-radical polymerization of acrylic acid alone or in combination with other ethylenically unsaturated monomers. The polymers can be synthesized by solvent/precipitation as well as emulsion polymerization techniques.

Another particularly preferred rheology modifying polymer of the present invention is a crosslinked anionic acrylate polymer. Said crosslinked anionic acrylate polymer may be contained in an aqueous dispersion comprising about 32% by weight of total solids. Examples of the crosslinked anionic acrylate polymer of the present invention include, but are not limited to, the polymer known by the INCI name acrylates crosspolymer-4 and commercially available from the supplier Lubrizol, under the tradename Carbopol® Aqua SF-2, as an aqueous dispersion comprising about 32% by weight of total solids. Acrylates Crosspolymer-4 may also be described as a copolymer of acrylic acid, methacrylic acid or one of its simple esters, crosslinked with trimethylolpropane triacrylate.

Thus, in some embodiments, the rheology modifying polymer of the present invention is selected from a slightly crosslinked, alkali-swellable acrylate polymer contained in an aqueous dispersion from comprising about 30% by weight of total solids.

In other embodiments, the rheology modifying polymer of the present invention is selected from a crosslinked anionic acrylate polymer contained in an aqueous dispersion from comprising about 32% by weight of total solids.

In yet other embodiments, the rheology modifying polymer of the present invention is chosen from a slightly crosslinked, alkali-swellable acrylate polymer contained in an aqueous dispersion from comprising about 30% by weight of total solids, a crosslinked anionic acrylate polymer contained in an aqueous dispersion from comprising about 32% by weight of total solids, and mixtures thereof.

In preferred embodiments, the at least one rheology modifying polymer of the present invention is neutralized in a water or an aqueous solution with a neutralizing agent before the polymer is added into the color base composition of the present invention.

In other preferred embodiments, the at least one rheology modifying polymer of the present invention is neutralized with a neutralizing agent at the time of addition of the polymer into the color base composition of the present invention.

Suitable neutralizing agents are chosen from organic amines, organic amine salts, and ammonium salts, particularly from ethylamines, ethyleneamines, alkanolamines, cyclic amines and other cyclic compounds, saturated or unsaturated, having one or more nitrogen atoms within the ring.

The neutralizing agent is employed in an amount sufficient to neutralize the rheology modifying polymer of the present invention in a water or an aqueous solution such that the solution becomes clear.

The at least one rheology modifying polymer of the present invention may be employed in an amount of from about 0.3% to about 3% by weight, such as from about 0.45% to about 2.75% by weight, further such as from about 0.5% to about 2% by weight, or such as about 2.55%, or such as about 1.95% by weight, based on the total weight of the color base composition of the present invention.

In preferred embodiments, the at least one fatty substance having a viscosity of greater than about 50 mm$^2$/s at 40° C. and the at least one rheology modifying polymer are present in the color base composition such that the weight ratio of said fatty substance to the rheology modifying polymer ranges from about 25:1 to about 3:1, or such as from about 22.5:1 to about 5:1, or such as from about 20:1 to about 10:1, preferably from about 15:1 to about 10:1, or such as from about 10:1 to about 5:1.

Alkalizing Agents

The alkalizing agent of the present invention may be chosen from organic amines, organic amine salts, ammonium salts, inorganic bases, and hydroxide base compounds.

The organic amines may be chosen from the ones having a pKb at 25° C. of less than 12, such as less than 10 or such as less than 6. It should be noted that this is the pKb corresponding to the function of highest basicity.

Organic amines may be chosen from organic amines comprising one or two primary, secondary, or tertiary amine functions, and at least one linear or branched $C_1$-$C_8$ alkyl groups bearing at least one hydroxyl radical.

Organic amines may also be chosen from alkanolamines such as mono-, di- or trialkanolamines, comprising one to three identical or different $C_1$-$C_4$ hydroxyalkyl radicals, ethylamines, ethyleneamines, quinoline, aniline and cyclic amines, such as pyrroline, pyrrole, pyrrolidine, imidazole, imidazolidine, imidazolidinine, morpholine, pyridine, piperidine, pyrimidine, piperazine, triazine and derivatives thereof.

Among the compounds of the alkanolamine type that may be mentioned include but not limited to: monoethanolamine (also known as monoethanolamine or MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, 2-amino-2-methyl-1-propanol, and tris(hydroxymethylamino)methane.

The organic amines correspond to the formula (IV):

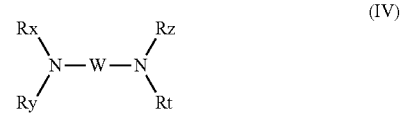

wherein W is chosen from $C_1$-$C_6$ alkylene residues optionally substituted with a hydroxyl group or a $C_1$-$C_6$ alkyl radical; Rx, Ry, Rz and Rt, which may be identical or different, are chosen from a hydrogen atom, $C_1$-$C_6$ alkyl radicals, $C_1$-$C_6$ hydroxyalkyl radicals, and $C_1$-$C_6$ aminoalkyl radicals.

Examples of such amines that may be mentioned include but not limited to: 1,3-diaminopropane, 1,3-diamino-2-propanol, spermine, and spermidine.

In some embodiments, the organic amines are chosen from amino acids.

As non-limiting examples, the amino acids that may be used may be of natural or synthetic origin, in L, D, or racemic form, and comprise at least one acid function chosen from, for instance, carboxylic acid, sulfonic acid, phosphonic acid, and phosphoric acid functions. The amino acids may be in their neutral or ionic form.

Further as non-limiting examples, the amino acids may be chosen from basic amino acids comprising an additional amine function optionally included in a ring or in a ureido function.

Such basic amino acids may be chosen from those corresponding to formula (A) below:

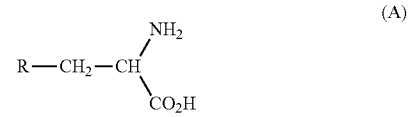

wherein R is a group chosen from:

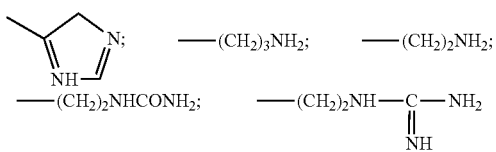

The compounds corresponding to formula (A) may be chosen from histidine, lysine, arginine, ornithine, and citrulline.

Amino acids that may be used in the present disclosure include but not limited to: aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine, and valine.

In some embodiments, the organic amines are chosen from basic amino acids. The amino acids may be chosen from, for instance, arginine, lysine and histidine, or mixtures thereof.

In some embodiments, the organic amines are chosen from organic amines of heterocyclic type. Besides histidine that has already been mentioned in the amino acids, non-limiting mention may also be made of pyridine, piperidine, imidazole, 1,2,4-triazole, tetrazole, and benzimidazole.

In some embodiments, the organic amines are chosen from amino acid dipeptides. Amino acid dipeptides that may be used in the present disclosure include but not limited to: carnosine, anserine, and baleine.

In some embodiments, the organic amines are chosen from compounds comprising a guanidine function. Organic amines of this type that may be used in the present disclosure include, besides arginine that has already been mentioned as an amino acid, creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

As a non-limiting example, the organic amines are chosen from alkanolamines. For example, the organic amines are chosen from ethanolamine, triethanoloamine, 2-amino-2-methyl-1-propanol, or preferably from 2-amino-2-methyl-1-propanol and monoethanolamine, or mixtures thereof. Further as an example, the organic amine is monoethanolamine.

The alkalizing agent may be an organic amine in salt form. The term "organic amine salt," as used herein, means organic or mineral salts of an organic amine as described above.

As a non-limiting example, the organic salts may be chosen from the salts of organic acids, such as citrates, lactates, glycolates, gluconates, acetates, propionates, fumarates, oxalates and tartrates.

Further as a non-limiting example, the mineral salts may be chosen from hydrohalides (for example hydrochlorides), carbonates, hydrogen carbonates, sulfates, hydrogen phosphates, and phosphates.

The ammonium salts that may be used according to the present disclosure may be chosen from the following acid salts: carbonate, bicarbonate. For instance, the salt is the carbonate, such as ammonium carbonate.

The inorganic bases that may be used may be chosen from alkali metal phosphates and carbonates such as, for example, sodium phosphate, potassium phosphate, sodium carbonate, sodium bicarbonate, potassium carbonate, potassium bicarbonate, and their derivatives.

The inorganic bases may also include alkali metals of carboxylates such as, for example, sodium acetate, potassium acetate, sodium citrate, and potassium citrate, and their derivatives.

The hydroxide base compounds can be chosen from alkali metal hydroxides, alkaline-earth metal hydroxides, transition metal hydroxides, quaternary ammonium hydroxides, organic hydroxides, and mixtures thereof. Suitable examples are ammonium hydroxide, sodium hydroxide, potassium hydroxide, lithium hydroxide, rubidium hydroxide, caesium hydroxide, francium hydroxide, beryllium hydroxide, magnesium hydroxide, calcium hydroxide, strontium hydroxide, barium hydroxide, molybdenum hydroxide, manganese hydroxide, zinc hydroxide, cobalt hydroxide, cadmium hydroxide, cerium hydroxide, lanthanum hydroxide, actinium hydroxide, thorium hydroxide, aluminium hydroxide, guanidinium hydroxide and mixtures thereof.

According to at least one embodiment, the alkalizing agent is chosen from alkali metal carbonates, alkali metal phosphate, organic amines, hydroxide base compounds, and derivatives thereof.

According to at least one embodiment, the alkalizing agent is chosen from at least one organic amine such as at least one alkanolamine. A particularly preferred alkanolamine is ethanolamine (also known as monoethanolamine or MEA).

The at least one alkalizing agent of the present invention may be employed in an amount of from about 0.01% to about 30% by weight, such as from about 0.1% to about 20% by weight, and further such as from about 0.5% to about 10% by weight, preferably from about 0.5% to about 5%, based on the total weight of the color base composition of the present invention.

In certain embodiments, a portion of the alkalizing agent is used to neutralize the at least one rheology modifying polymer before or after the polymer is added during the process of making the color base composition.

According to at least one embodiment, the compositions or agents for altering the color of keratin fibers of the present invention contain a small amount of ammonia, or is substantially free of ammonia.

Short Chain Hydroxy Compounds

The at least one short alkyl chain hydroxy compound chosen from monoalcohols and polyols of the present invention includes, but is not limited to, ethanol (alcohol denatured), propanol, ethylene glycol, propylene glycol, butylene glycol, hexylene glycol, propane diol, glycerin, and mixtures thereof.

As used herein, the term "short alkyl chain" refers to an alkyl chain having from 1 to 10 carbon atoms.

Thus, the at least one short alkyl chain hydroxy compound are chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3-butylene glycol, dipropylene glycol, butylene glycol, hexylene glycol, caprylyl glycol and glycerin.

Other suitable short alkyl chain hydroxy compounds chosen from monoalcohols and polyols can be volatile or non-volatile compounds.

The at least one short alkyl chain hydroxy compound chosen from monoalcohols and polyols may be employed according to the present invention in an amount ranging from about 0.5% to about 15% by weight, such as from about 1% to about 12% by weight, or such as from about 3% to about 10% by weight, or such as from about 5% to about 10% by weight, based on the total weight of the color base composition of the present invention.

Oxidative Dye Precursors

Typically the oxidative dye precursors are selected from ortho- or para-phenylenediamines, ortho- or para-aminophenols and heterocyclic compounds. These oxidation bases are colourless or lightly coloured compounds which, in combination with oxidizing products, allow coloured species to be obtained, by a process of oxidative condensation.

Useful oxidative dye precursors of the present disclosure include, by way of example only, aromatic diamines, polyhydric phenols, amino phenols, and derivatives of these compounds, such as, for example, N-substituted derivatives of the amines, and ethers of the phenols.

By way of non-limiting example, oxidative dye precursors may be chosen from ortho- or para-aminophenols, ortho- or para-phenylenediamines, double bases, heterocyclic bases, and the acid addition salts thereof.

Exemplary para-phenylenediamines which may be chosen include compounds of the general formula (IV) and their addition salts with an acid:

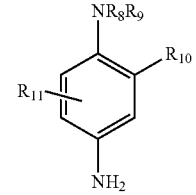

wherein, in formula (IV):
R8 represents a hydrogen atom, a C1-C4 alkyl radical, a C1-C4 monohydroxyalkyl radical, a C2-C4 polyhydroxyalkyl radical, a (C1-C4)alkoxy(C1-C4)alkyl radical, a C1-C4 alkyl radical substituted by a nitrogenous group, a phenyl radical or a 4'-aminophenyl radical;

R9 represents a hydrogen atom, a C1-C4 alkyl radical, a C1-C4 monohydroxyalkyl radical, a C2-C4 polyhydroxyalkyl radical, a (C1-C4)alkoxy(C1-C4)alkyl radical or a C1-C4 radical substituted by a nitrogenous group;

R8 and R9 can also form, with the nitrogen atom which carries them, a 5- or 6-membered nitrogenous heterocycle optionally substituted by one or more alkyl, hydroxyl or ureido groups;

R10 represents a hydrogen atom, a halogen atom, such as a chlorine atom, a C1-C4 alkyl radical, a sulpho radical, a carboxyl radical, a C1-C4 monohydroxyalkyl radical, a C1-C4 hydroxyalkoxy radical, a C1-C4 acetylaminoalkoxy radical, a C1-C4 mesylaminoalkoxy radical or C1-C4 carbamoylaminoalkoxy radicals; and R11 represents a hydrogen atom, a halogen atom or a C1-C4 alkyl radical.

By way of example, among the nitrogenous groups in the above formula (IV), of the amino, mono(C1-C4)alkylamino, di(C1-C4)alkylamino, tri(C1-C4)alkylamino, monohydroxy(C1-C4)alkylamino, imidazolinium and ammonium radicals may be chosen. Exemplary para-phenylenediamines of above formula (XXIII), include para-phenylenediamine, para-toluoylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(beta-hydroxyethyl)-para-phenylenediamine, 4-N,N-bis(beta-hydroxyethyl)amino-2-methylaniline, 4-N,N-bis(beta-hydroxyethyl)amino-2-chloroaniline, 2-(beta-hydroxyethyl)-para-phenylenediamine, 2-fluoro-para-phenylenediamine, 2-isopropyl-para-phenylenediamine, N-(beta-hydroxypropyl)-para-phenylenediamine, 2-hydroxymethyl-para-phenylenediamine, N,N-dimethyl-beta-methyl-para-phenylenediamine, N-ethyl-N-(beta-hydroxyethyl)-para-phenylenediamine, N-(beta,gamma-dihydroxypropyl)-para-phenylenediamine, N-(4'-aminophenyl)-para-phenylenediamine, N-phenyl-para-phenylenediamine, 2-((beta-hydroxyethyloxy)-para-phenylenediamine, 2-((beta-acetylaminoethyloxy)-para-phenylenediamine, N-(beta-methoxyethyl)-para-phenylenediamine, 2-methyl-1-N-(beta-hydroxyethyl)-para-phenylenediamine and their addition salts with an acid.

Exemplary ortho-phenylenediamines, include N1-(2-hydroxyethyl)-4-nitro-o-phenylenediamine, 4-methyl-o-phenylenediamine, and 4-nitro-o-phenylenediamine and acid addition salts thereof.

As used herein, the term "double bases" means compounds comprising at least two aromatic nuclei having at least one of amino and hydroxyl groups. For example, double bases may be chosen from compounds of the formula (V) and their addition salts with an acid:

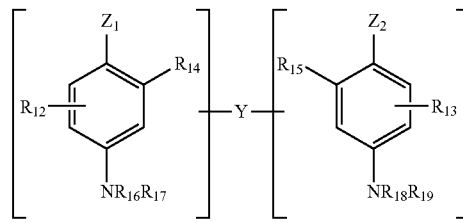

wherein, in formula (V):

Z1 and Z2 may independently be chosen from a hydroxyl or —NH2 radical which can be substituted by a C1-C4 alkyl radical or by a connecting arm Y;

the connecting arm Y is chosen from a linear or branched alkylene chain comprising from 1 to 14 carbon atoms which can be interrupted or terminated by one or more nitrogenous groups and/or by one or more heteroatoms, such as oxygen, sulphur or nitrogen atoms, and which is optionally substituted by one or more hydroxyl or C1-C6 alkoxy radicals;

R12 and R13 are independently chosen from a hydrogen or halogen atom, a C1-C4 alkyl radical, a C1-C4 monohydroxyalkyl radical, a C2-C4 polyhydroxyalkyl radical, a C1-C4 aminoalkyl radical or a connecting arm Y;

R14, R15, R16, R17, R18 and R19 are independently chosen from a hydrogen atom, a connecting arm Y or a C1-C4 alkyl radical;

wherein compounds of formula (V) only comprise a single connecting arm Y per molecule.

In various embodiments, nitrogenous groups of the above formula (V), may be chosen from amino, mono(C1-C4)alkylamino, di(C1-C4)alkylamino, tri(C1-C4)alkylamino, monohydroxy(C1-C4)alkylamino, imidazolinium and ammonium radicals.

Nonlimiting examples of double bases include N,N'-bis(beta-hydroxyethyl)-N,N'-bis(4'-aminophenyl)-1,3-diamino-propan-ol, N,N'-bis(beta-hydroxyethyl)-N,N'-bis(4'-aminophenyl)ethylenediamine, N,N'-bis(beta-aminophenyl)-tetramethylenediamine, N,N'-bis(4-hydroxyethyl)-N,N'-bis(4-aminophenyl) tetramethylenediamine, N,N'-bis(4-methylaminophenyl) tetramethylenediamine, N,N'-diethyl-N,N'-bis(4'-amino-3'-methylphenyl)ethylenediamine, 1,8-bis(2,5-diaminophenoxy)-3,5-dioxaoctane, and their addition salts with an acid.

Non-limiting examples of para-aminophenols which can be used in the context of the invention can be chosen in particular from the compounds corresponding to the following formula (VI): and their addition salts with an acid:

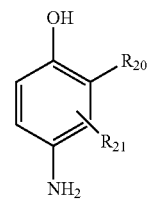

wherein, in formula (VI):

R20 is chosen from a hydrogen atom, a halogen atom, such as fluorine, a C1-C4 alkyl radical, a C1-C4 monohydroxyalkyl radical, a (C1-C4)alkoxy(C1-C4)alkyl radical, a C1-C4 aminoalkyl radical or a hydroxy(C1-C4) alkylamino-(C1-C4)alkyl radical, and R21 is chosen from a hydrogen atom, a halogen atom, such as fluorine, a C1-C4 alkyl radical, a C1-C4 monohydroxyalkyl radical, a C2-C4 polyhydroxyalkyl radical, a C1-C4 aminoalkyl radical, a C1-C4 cyanoalkyl radical or a (C1-C4)alkoxy(C1-C4)alkyl radical.

By way of example only, para-aminophenol, 4-amino-3-methylphenol, 4-amino-3-fluorophenol, 4-amino-3-hydroxymethylphenol, 4-amino-2-methylphenol, 4-amino-2-hydroxymethyl phenol, 4-amino-2-methoxymethylphenol, 4-amino-2-aminomethylphenol, 4-amino-2-(beta-hydroxyethylaminomethyl)phenol, N-methyl-para-aminophenol, and the acid addition salts thereof may be chosen.

Exemplary ortho-aminophenols may be chosen from 2-aminophenol, 2-amino-1-hydroxy-5-methylbenzene, 2-amino-1-hydroxy-6-methylbenzene, 5-acetamido-2-aminophenol, and the acid addition salts thereof.

Exemplary heterocyclic bases may be chosen from pyridine derivatives, pyrimidine derivatives, pyrazole derivatives, pyrazolinone derivatives, and the acid addition salts thereof.

Non-limiting examples of pyridine derivatives include, for example, those disclosed in GB1026978 and GB1153196, both incorporated by reference herein, such as 2,5-diaminopyridine, 2-(4-methoxyphenyl)amino-3-aminopyridine, 2,3-diamino-6-methoxypyridine, 2-(beta-methoxyethyl)amino-3-amino-6 methoxypyridine, 3,4-diaminopyridine, and the acid addition salts thereof.

Non-limiting examples of pyrimidine derivatives include, for example, those described in DE 2 359 399, JP 88-169 571, JP 91-10659 and WO 96/15765, all incorporated by reference herein, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolopyrimidine derivatives, such as those mentioned in French Application FR-A-2 750 048 and among which may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; 3-amino-5-methyl-7-(imidazolylpropylamino)pyrazolo[1,5-a]pyrimidine; and their addition salts and their tautomeric forms, when there exists a tautomeric equilibrium, and their addition salts with an acid.

Non-limiting examples of pyrazole and pyrazolinone derivatives include the compounds described in DE 3,843,892, DE 4,133,957, WO 94/08969, WO 94/08970, FR-A-2,733,749, and DE 195 43 988, all of which are incorporated by reference herein, such as 4,5-diamino-1-methyl-pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(beta-hydroxyethyl)-3-methylpyrazole, 4,5-diamino-1-(beta-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(p-hydroxyethyl)amino-1-methylpyrazole, 2-(4,5-diamino-1H-pyrazol-1-yl), H2SO4, 2,3-diamino-6,7-dihydro-1H,5H-pyrazolo[1,2-z]pyrazol-1-one, 1-methyl-3-phenyl-2-pyrazolinone, and the acid addition salts thereof.

The at least one oxidation dye precursor may be present in the color base composition of the present disclosure in an amount ranging from, for example, about 0.0001% to about 12%, such as from about 0.0001% to about 8.0%, or from about 0.005% to about 5% by weight, based on the total weight of the color base composition.

Furthermore, one or more oxidative dye precursors of the present disclosure may be employed in combination with one or more couplers.

The shades obtained with the use of oxidative dye precursors are very often varied by combining them with one or more couplers, the latter being selected in particular from aromatic meta-diamines, meta-aminophenols, meta-diphenols and certain heterocyclic compounds, such as indole compounds.

The variety of the molecules employed for the oxidation bases and couplers allows a rich palette of colours to be obtained.

The couplers that may be used in the present disclosure include those conventionally used in oxidative methods of coloring keratinous fibers, for example, meta-aminophenols, meta-phenylenediamines and meta-diphenols, naphthols, mono- or polyhydroxylated naphthalene derivatives, and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, benzomorpholine derivatives, pyrazoloazole derivatives, pyrroloazole derivatives, imidazoloazole derivatives, pyrazolopyrimidine derivatives, pyrazoline-3,5-dione derivatives, pyrrolo[3,2-d]oxazole derivatives, pyrazolo[3,4-d]thiazole derivatives, thiazoloazole S-oxide derivatives, thiazoloazole S,S-dioxide derivatives, and the acid addition salts thereof.

Suitable color couplers include, for example, those having the general formula (D):

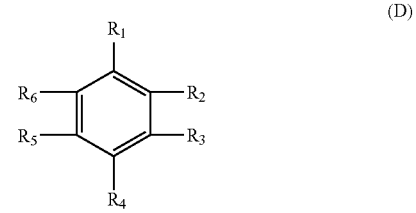

(D)

wherein $R_1$ is unsubstituted hydroxy or amino, or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ hydroxyalkyl, or $C_{1-6}$ alkyl, or $R_3$ and $R_4$ together may form a methylenedioxy or ethylenedioxy group. Examples of such compounds include meta-derivatives such as phenols, meta-aminophenols, meta-phenylenediamines, and the like, which may be unsubstituted, or substituted on the amino group or benzene ring with alkyl, hydroxyalkyl, alkylamino groups, and the like. Suitable couplers include m-aminophenol, 2,4-diaminotoluene, 4-amino, 2-hydroxytoluene, phenyl methyl pyrazolone, 3,4-methylenedioxyphenol, 3,4-methylenedioxy-1-[(β-hydroxyethyl)amino]benzene, 1-methoxy-2-amino-4-[(β-hydroxyethyl)amino]benzene, 1-hydroxy-3-(dimethylamino)benzene, 6-methyl-1-hydroxy-3[(β-hydroxyethyl)amino]benzene, 2,4-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(β-hydroxyethyl)amino-3-aminobenzene, 2-methyl-1,3-diaminobenzene, 6-methoxy-1-amino-3-[(β-hydroxyethyl)amino]-benzene, 6-(β-aminoethoxy)-1,3-diaminobenzene, 6-(β-hydroxyethoxy)-1-amino-3-(methylamino)benzene, 6-carboxymethoxy-1,3-diaminobenzene, 6-ethoxy-1-bis(β-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino)benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, 2,4-diaminophenoxyethanol, and mixtures thereof.

Other couplers may be chosen, for example, from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino 1-(β-hydroxyethyloxy)benzene, 2-amino-4-(R-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole, 2,6-dimethylpyrazolo[1,5-b]-1,2,4-triazole, 6-methyl pyrazolo[1,5-a]-benzimidazole, and the acid addition salts thereof.

In one embodiment, the couplers include resorcinol, 1-naphthol, 2-methylresorcinol, 4-amino-2-hydroxy toluene, m-aminophenol, 2,4-diaminophenoxyethanol, phenyl methyl pyrazolone, hydroxybenzomorpholine, 2-methyl-5-hydroxyetyylaminophenol, 6-hydroxyindole, 2-amino-3-hydroxypyridine, 5-amino-6-chloro-o-cresol, 4-chlororesorcinol, their salts, and mixtures thereof.

When they are present, couplers may be present in amounts ranging from about 0.0001% to about 12% by weight; or from about 0.1% to about 8% by weight; or from about 1% to about 5% based on the total weight of the color base composition.

In general, the acid addition salts of the oxidation bases and couplers may be chosen from hydrochlorides, hydrobromides, sulphates, tartrates, lactates, and acetates.

The color base composition of the present invention can further comprise at least one direct dye, which can include, but are not limited to, nitro dyes of the benzene series, the azo direct dyes, the methane direct dyes, and addition salts thereof. These direct dyes can be of non-ionic, anionic, or cationic character.

Oxidizing Agent

The agent for altering the color of keratin fibers of the present invention requires an oxidizing composition including at least one oxidizing agent which may be chosen, for example, from a peroxide, a persulfate, a perborate, a percarbonate, alkali metal bromates, ferricyanides or a mixture thereof. Oxidizing agents that may also be used include at least one redox enzyme such as laccases, peroxidases, and 2-electron oxidoreductases, such as uricase, where appropriate in the presence of their respective donor or co-factor. Oxygen in the air may also be employed as an oxidizing agent.

In one embodiment, the oxidizing agent is chosen from hydrogen peroxide, urea peroxide, alkali metal bromates, ferricyanides, peroxygenated salts, perborates, percarbonates, laccases, peroxidases, redox enzymes, and mixtures thereof.

In one embodiment, the oxidizing agent is hydrogen peroxide present in an aqueous solution whose titre may range from 1 to 40 volumes, such as from 5 to 40 volumes or such as from 5 to 20 volumes.

In another embodiment, the oxidizing agent is a persulfate and/or a monopersulfate such as, for example, potassium persulfate, sodium persulfate, ammonium persulfate, as well as mixtures thereof. In one embodiment the oxidizing agents in the present disclosure are selected from hydrogen peroxide, potassium persulfate, sodium persulfate and mixtures thereof.

In general, the oxidizing agent will be present in an amount of from about 0.05 to about 50% by weight, such as from about 0.1% to about 30% by weight, or such as from about 0.1% to about 20% by weight, or such as from about 1% to about 12% by weight, based on the total weight of the oxidizing composition.

Cosmetically Acceptable Medium

The compositions of the present invention can comprise other compounds constituting the cosmetically acceptable medium. This cosmetically acceptable medium comprises water or a mixture of water and at least one cosmetically acceptable organic solvent.

As examples of organic solvents, non-limiting mentions can be made of alcohols such as ethyl alcohol, isopropyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

pH

The pH of the color base composition is greater than 7 and may range from about 7.1 to about 14, or such as from about 7.5 to about 12, or such as from about 7.5 to about 11, or such as from about 7.5 to about 10 or such as from about 7.5 to about 9, or such as from about 9 to about 11, or such as from about greater than 7 but less than 9, and it may be adjusted to the desired value using acidifying or basifying agents that are well known in the art in the dyeing of keratin fibers.

In addition, the pH of the agent for altering the color of keratin fibers, i.e., the composition resulting from mixing together the color base composition and the oxidizing composition, ranges from about 1 to about 7, or such as from about 1 to 6.9, or such as from about 2 to 6.8, or such as from about 2 to about 6.5, or such as from about 4 to about 6.0.

The color base composition of the present disclosure is preferably in the form of an emulsion, for example, oil-in-water emulsion and water-in-oil emulsion.

In particularly preferred embodiments, the color base composition of the present disclosure is preferably in the form of an oil-in-water emulsion.

The color base and oxidizing compositions of the present invention may further comprise at least one auxiliary agent. The auxiliary agent may include, but is not limited to thickening agents and rheology modifying polymers other than those described above (such as those commercially available as Carbopol® Aqua SF-1 and Carbopol® Aqua SF-2), cationic polymers, film forming polymers, pigments, dyes, humectants and moisturizing agents, emulsifying agents other than those that fall under the above-described fatty substances, structuring agents, propellants, surfactants, shine agents, and conditioning agents.

Thickening agents and rheology modifying polymers other than the above-described rheology modifying polymers (such as those commercially available as Carbopol® Aqua SF-1 and Carbopol® Aqua SF-2) may further comprise the compositions of the present invention and may be chosen from polymeric thickeners and non-polymeric thickeners as described in US2010154140A, herein incorporated by reference in its entirety.

Thickening agents of the present invention may be chosen from polymeric thickeners and non-polymeric thickeners. The at least one polymeric thickener can be chosen from ionic or non-ionic, associative or non-associative polymers. Exemplary polymeric thickeners include various native gums. Representative non-polymeric thickening agents include mineral salts such as sodium chloride; oxyethylenated molecules and especially ethoxylated alkyl or acyl derivatives of polyols. These polymers can be modified physically or chemically.

The at least one thickening agent of the present invention is preferably used in an amount of from greater than 0% to about 15% by weight, preferably from about 0.1% to about 10% by weight, and more preferably from about 1% to about 5% by weight, based on the total weight of the color base or oxidizing composition of the present invention.

The color base and oxidizing compositions according to the present invention can also comprise at least one cationic polymer.

In at least one embodiment, the at least one cationic polymer included in the compositions of the disclosure is not chosen from cationic associative polymers. In other words, these cationic polymers do not comprise in their structure a pendent or terminal hydrophobic chain, for example of alkyl or alkenyl type, containing from 10 to 30 carbon atoms.

The at least one cationic polymer of the compositions according to the disclosure can be chosen from, for example:

(1) homopolymers and copolymers derived from acrylic or methacrylic esters or amides and comprising at least one unit chosen from units of formulae (VI), (VII), (VIII) and (IX):

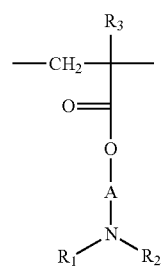

(VI)

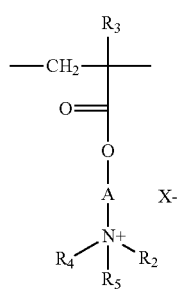

(VII)

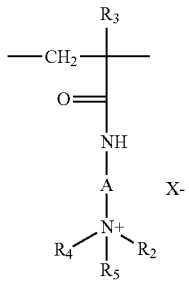

(VIII)

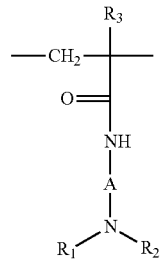

(IX)

wherein:
$R_3$ which may be identical or different, denotes a hydrogen atom or a $CH_3$ radical;
A, which may be identical or different, represents a linear or branched $C_1$-$C_6$ and, for example, $C_2$-$C_3$ alkyl group or a $C_1$-$C_4$ hydroxyalkyl group;
$R_4$, $R_5$ and $R_6$, which may be identical or different, represent a $C_1$-$C_{18}$ alkyl group or a benzyl radical, such as a $C_1$-$C_6$ alkyl group;
$R_1$ and $R_2$, which may be identical or different, represent hydrogen or a $C_1$-$C_6$ alkyl group, for example methyl or ethyl;
$X^-$ denotes an anion derived from a mineral or organic acid, such as a methosulfate anion or a halide such as chloride or bromide.

The polymers of this family can also contain at least one unit derived from at least one comonomer which may be chosen from the family of acrylamides, methacrylamides, diacetone acrylamides, acrylamides and methacrylamides substituted on the nitrogen with lower ($C_1$-$C_4$)alkyls, acrylic or methacrylic acids or esters thereof, vinyllactams such as vinylpyrrolidone or vinylcaprolactam, and vinyl esters.

Thus, among the polymers of this family, exemplary mention may be made of:

copolymers of acrylamide and of dimethylaminoethyl acrylate quaternized with dimethyl sulfate or with a dimethyl halide, such as the product sold under the name HERCOFLOC by the company Hercules, the copolymers of acrylamide and of methacryloyloxyethyltrimethylammonium chloride described, for example, in EP 80 976 and sold under the name BINA QUAT P 100 by the company Ciba Geigy, the copolymer of acrylamide and of methacryloyloxyethyltrimethylammonium methosulfate sold under the name RETEN by the company Hercules, quaternized or non-quaternized vinylpyrrolidone/dialkylaminoalkyl acrylate or acrylate copolymers, such as the products sold under the name GAFQUAT by the company ISP, for instance GAFQUAT 734 or GAFQUAT 755, or alternatively the products known as COPOLYMER 845, 958 and 937, dimethylaminoethyl acrylate/vinylcaprolactam/vinylpyrrolidone terpolymers, such as the product sold under the name GAFFIX VC 713 by the company ISP, vinylpyrrolidone/methacrylamidopropyldimethylamine copolymers sold, for example, under the name STYLEZE CC 10 by ISP, quaternized vinylpyrrolidone/dimethylaminopropylmethacrylamide copolymers such as the product sold under the name GAFQUAT HS 100 by the company ISP, and crosslinked polymers of methacryloyloxy($C_1$-$C_4$)alkyltri($C_1$-$C_4$)alkylammonium salts such as the polymers obtained by homopolymerization of dimethylaminoethyl acrylate quaternized with methyl chloride, or by copolymerization of acrylamide with dimethylaminoethyl acrylate quaternized with methyl chloride, the homo- or copolymerization being followed by crosslinking with a compound containing olefinic unsaturation, such as methylenebisacrylamide. In at least one embodiment, a crosslinked acrylamide/methacryloyloxyethyltrimethylammonium chloride copolymer (20/80 by weight) in the form of a dispersion containing 50% by weight of the copolymer in mineral oil can be used. This dispersion is sold under the name SALCARE® SC 92 by the company Ciba. In some embodiments, a crosslinked methacryloyloxyethyltrimethylammonium chloride homopolymer containing about 50% by weight of the homopolymer in mineral oil or in a liquid ester can be used. These dispersions are sold under the names SALCARE® SC 95 and SALCARE® SC 96 by the company Ciba.

Other examples are cellulose ether derivatives comprising quaternary ammonium groups, such as the polymers sold under the names JR (JR 400, JR 125, JR 30M) or LR (LR 400, LR 30M) by the company Union Carbide Corporation.

(2) copolymers of cellulose or cellulose derivatives grafted with a water-soluble quaternary ammonium monomer, such as hydroxymethyl-, hydroxyethyl- or hydroxy-propylcelluloses grafted, for instance, with a methacryloylethyltrimethylammonium, methacrylamidopropyltrimethylammonium or dimethyldiallylammonium salt. These are sold under the name CELQUAT L 200 and CELQUAT H 100 by the company National Starch.

(3) non-cellulose cationic polysaccharides, such as guar gums containing trialkylammonium cationic groups. Such products are sold, for example, under the trade names JAGUAR C13S, JAGUAR C15, JAGUAR C17 and JAGUAR C162 by the company Meyhall.

(4) polymers of piperazinyl units and of divalent alkylene or hydroxyalkylene radicals.

(5) water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in an amount ranging from 0.025 to 0.35 mol per amine group of the polyamino amide; these polyamino amides can be alkylated or, if they contain at least one tertiary amine function, they can be quaternized. Exemplary mention may be made of the adipic acid/dimethylaminohydroxypropyl/diethylenetriamine polymers sold under the name CARTARETINE F, F4 or F8 by the company Sandoz.

(6) the polymers obtained by reaction of at least one polyalkylene polyamine containing two primary amine groups and at least one secondary amine group with a dicarboxylic acid chosen from diglycolic acid and saturated $C_3$-$C_8$ aliphatic dicarboxylic acids. The molar ratio between the polyalkylene polyamine and the dicarboxylic acid ranges from 0.8:1 to 1.4:1; the polyamino amide resulting therefrom is reacted with epichlorohydrin in a molar ratio of epichlorohydrin relative to the secondary amine group of the polyamino amide ranging from 0.5:1 to 1.8:1. Polymers of this type are sold, for example, under the name HERCOSETT 57, PD 170 or DELSETTE 101 by the company Hercules.

(7) cyclopolymers of alkyldiallylamine and of dialkyldiallylammonium, such as the homopolymers or copolymers containing, as main constituent of the chain, at least one unit corresponding to formula (X) or (XI):

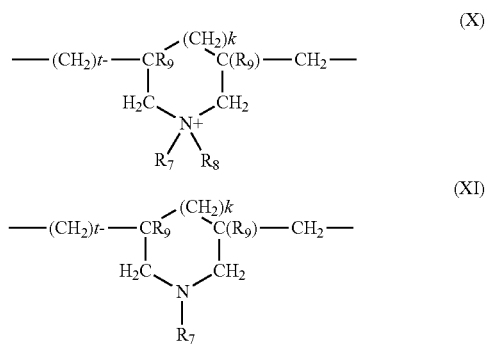

wherein formulae k and t are equal to 0 or 1, the sum k+t being equal to 1; $R_9$ denotes a hydrogen atom or a methyl radical; $R_7$ and $R_8$, independently of each other, denote a $C_1$-$C_8$ alkyl group, a hydroxyalkyl group in which the alkyl group is $C_1$-$C_5$, an amidoalkyl group in which the alkyl is $C_1$-$C_4$; or $R_7$ and $R_8$ denote, together with the nitrogen atom to which they are attached, a heterocyclic group such as piperidyl or morpholinyl; in at least one embodiment $R_7$ and $R_8$, independently of each other, denote a $C_1$-$C_4$ alkyl group; $Y^-$ is an organic or mineral anion such as bromide, chloride, acetate, borate, citrate, tartrate, bisulfate, bisulfite, sulfate or phosphate.

Among the polymers defined above, exemplary mention may be made of the dimethyldiallylammonium chloride homopolymer sold under the name MERQUAT® 100 and MERQUAT® 280 by the company Nalco (and its homologues of low weight-average molecular mass) and the copolymers of diallyldimethylammonium chloride and of acrylamide, sold under the name MERQUAT® 550.

(8) quaternary diammonium polymers containing repeating units of formula (XII):

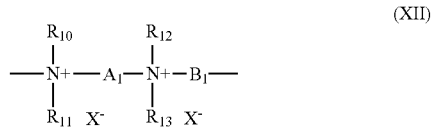

wherein:

$R_{10}$, $R_{11}$, $R_{12}$ and $R_{13}$, which may be identical or different, represent $C_1$-$C_6$ aliphatic, alicyclic or arylaliphatic radicals or hydroxyalkylaliphatic radicals wherein the alkyl radical is $C_1$-$C_4$, or alternatively $R_{10}$, $R_{11}$, $R_{12}$ and $R_{12}$, together or separately, constitute, with the nitrogen atoms to which they are attached, heterocycles optionally containing a second heteroatom other than nitrogen, or alternatively $R_{10}$, $R_{11}$, $R_{12}$ and $R_{13}$ represent a linear or branched $C_1$-$C_6$ alkyl radical substituted with a nitrile, ester, acyl or amide group or a group —CO—O—$R_{14}$-D or —CO—NH—$R_{14}$-D wherein $R_{14}$ is an alkylene and D is a quaternary ammonium group;

$A_1$ and $B_1$ represent $C_2$-$C_6$ polymethylene groups which are linear or branched, saturated or unsaturated, and which optionally contain, linked to or intercalated in the main chain, at least one aromatic ring or at least one atom chosen from oxygen and sulfur atom or at least one group chosen from sulfoxide, sulfone, disulfide, amino, alkylamino, hydroxyl, quaternary ammonium, ureido, amide and ester groups, and $X^-$ denotes an anion derived from a mineral or organic acid;

$A_1$, $R_{10}$ and $R_{12}$ can form, with the two nitrogen atoms to which they are attached, a piperazine ring;

and wherein, if $A_1$ denotes a linear or branched, saturated or unsaturated alkylene or hydroxyalkylene radical, $B_1$ can also denote a group —$(CH_2)_n$—CO-D-OC—$(CH_2)_n$— wherein n is a number ranging from 1 to 6, and D is chosen from:

a) a glycol residue of formula: —O—Z—O—, where Z denotes a linear or branched hydrocarbon-based radical or a group corresponding to one of the following formulae: —($CH_2$—$CH_2$—O)$_x$—$CH_2$—$CH_2$—; or —[$CH_2$—CH($CH_3$)—O]$_y$—$CH_2$—CH($CH_3$)—, where x and y denote an integer ranging from 1 to 4, representing a defined and unique degree of polymerization or any number ranging from 1 to 4 representing an average degree of polymerization;

b) a bis-secondary diamine residue such as a piperazine derivative;

c) a bis-primary diamine residue of formula: —NH—Y—NH—, wherein Y denotes a linear or branched hydrocarbon-based radical, or alternatively the radical —$CH_2$—$CH_2$—S—S—$CH_2$—$CH_2$—; and d) a ureylene group of formula: —NH—CO—NH—.

In at least one embodiment, $X^-$ is an anion such as chloride or bromide.

These polymers, for example, have a number-average molecular mass ranging from 1000 to 100,000.

In some embodiments, polymers are used that consist of repeating units corresponding to formula (XIII):

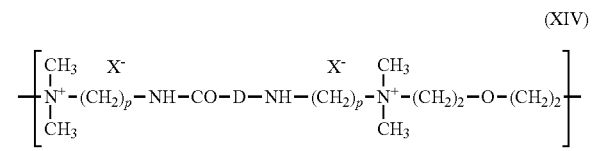

wherein $R_{10}$, $R_{11}$, $R_{12}$ and $R_{13}$, which may be identical or different, denote a $C_1$-$C_4$ alkyl or hydroxyalkyl radical, n and p are integers ranging from 2 to 6, and $X^-$ is an anion derived from a mineral or organic acid.

In at least one embodiment, the at least one cationic polymer corresponding to this family comprise repeating units of formulae (W) and (U):

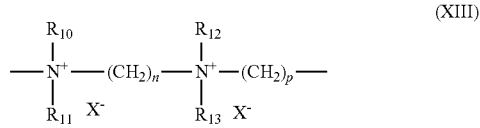

for example those whose molecular weight, determined by gel permeation chromatography, ranges from 9,500 to 9,900;

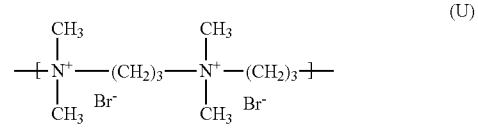

for instance those whose molecular weight, determined by gel permeation chromatography, is 1200.

(9) polyquaternary ammonium polymers consisting of repeating units of formula (XIV):

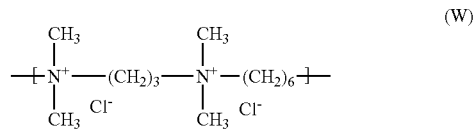

wherein p denotes an integer ranging from 1 to 6, D may be zero or may represent a group —$(CH_2)_r$—CO— wherein r denotes a number ranging from 1 to 6, and $X^-$ is an anion.

Such polymers may be prepared according to the processes described in U.S. Pat. Nos. 4,157,388, 4,702,906 and 4,719,282. They are described, for example, in patent application EP 122 324.

Among these polymers, examples that may be mentioned include the products MIRAPOL A 15, MIRAPOL AD1, MIRAPOL AZ1 and MIRAPOL 175 sold by the company Miranol.

(10) quaternary polymers of vinylpyrrolidone and of vinylimidazole, for instance the products sold under the names LUVIQUAT FC 905, FC 550 and FC 370 by the company BASF.

(11) vinylamide homopolymers or copolymers, such as partially hydrolysed vinylamide homopolymers such as poly(vinylamine/vinylamide)s.

(12) cationic polyurethane derivatives, for example those of elastic nature formed from the reaction:

(a1) of at least one cationic unit resulting from at least one tertiary or quaternary amine bearing at least two reactive functions containing labile hydrogen, (a2) of at least one mixture of at least two different nonionic units bearing at least two reactive functions containing labile hydrogen, for instance chosen from hydroxyl groups, primary or secondary amine groups, and thiol groups, and (b) of at least one compound comprising at least two isocyanate functions.

(13) Other cationic polymers that may be used in the context of the disclosure include, for example, cationic proteins or cationic protein hydrolysates, polyalkyleneimines, such as polyethyleneimines, polymers containing vinylpyridine or vinylpyridinium units, and chitin derivatives.

Particularly useful cationic polymers in the present invention include, but are not limited to, polyquaternium 4, polyquaternium 6, polyquaternium 7, polyquaternium 10, polyquaternium-11, polyquaternium-16, polyquaternium-22, polyquaternium-28, polyquaternium-32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride.

Particularly preferred cationic polymers of the present invention include POLYMER JR-125, POLYMER JR-400, Polymer JR-30M hydroxyethyl cellulosic polymers (polyquaternium 10) available from AMERCHOL; JAGUAR C® 13-S, guar hydroxypropyltrimonium chloride, available from Rhodia; and MERQUAT® 100 and 280, a dimethyl dialkyl ammonium chloride (polyquaternium 6) available from Nalco.

The cationic polymer is generally present in an amount of from greater than 0% to about 15%, preferably from about 0.5 to about 10% by weight, and more preferably from about 1 to about 5% by weight, based on the total weight of the color base or oxidizing composition.

The color base and oxidizing compositions of the present invention according to the disclosure can also comprise at least one additive used conventionally in compositions for application onto hair.

"Additive" means a substance that is added, different from the compounds already mentioned.

As examples of additives that can be used, non-limiting mentions can be made of antioxidants or reducing agents, penetrating agents, sequestering agents, perfumes, buffers, dispersants, ceramides, sunscreen agents, preservatives, opacifiers, and antistatic agents.

The oxidizing composition comprising at least one oxidizing agent can further comprise at least one fatty substance chosen from the above-described fatty substance, including the at least one fatty substance having a viscosity greater than about 50 mm$^2$/s at 40° C. Thus, in some embodiments, the total amount of fatty substances in the oxidizing composition may range from about 1% to about 20% by weight, or such as from about 5% to about 20% by weight, or such as from about 10% to about 20% by weight, based on the total weight of the oxidizing composition.

According to preferred embodiments of the invention, when the color base composition is mixed with the oxidizing composition, the total amount of fatty substances is at least about 1.25% by weight and may range up to less than about 50% by weight, or up to about 40% by weight, or up to about 30% by weight, or up to about 20% by weight, or up to about 10% by weight, based on the total weight of the agent for altering the color of keratin fibers formed from the combination of the color base and oxidizing compositions of the present invention.

The color base composition of the present disclosure is in the form of a water-in-oil cream emulsion.

The color base and oxidizing compositions according to the disclosure can be in various forms, such as in the form of creams or gel-creams.

In preferred embodiments, the process of making the color base composition, involves a cold process which does not require the use of heat while the ingredients are mixed and does not require the use of an emulsifier blade.

In other preferred embodiments, the color base composition does not require the presence of a fatty alcohol in order to form an emulsion. When the color base composition does not contain a fatty alcohol, the color base composition may be prepared in the absence of heat using mixing speeds at shearing rates that are lower than the shearing rates used to prepare conventional/commercial hair color that are typically provided in the form of emulsions.

According to the present disclosure, the process of making the color base composition involves the general procedure of:

mixing the acrylates copolymer of the present invention (e.g., Carbopol® Aqua SF-1 or Carbopol® Aqua SF-2) with water using a mixer, adding an amount of a neutralizing agent, such as ethanolamine, to the mixture, in order to neutralize the acrylates polymer (indicated by the formation of a clear solution), adding a high viscosity fatty substance (mineral oil having a viscosity greater than about 50 mm$^2$/s at 40° C.) while mixing with a chopper blade, wherein the speed of mixing can be increased to ensure proper mixing)

optionally, adding more of the high viscosity fatty substance if an emulsion is desired, adding a short alkyl chain hydroxyl compound (e.g. ethanol), and adding a pH adjusting agent to obtain the desired pH, if necessary.

The acrylates copolymer may also be pre-neutralized before it is combined with the other ingredients according to the process above.

The above-described process reduces the amount of time needed to prepare a conventional/commercial hair color base composition.

The process for coloring keratin fibers according to the present invention, comprises:

(1) applying onto keratin fibers, an agent for altering the color of keratin fibers as described above, wherein (A) and (B) are mixed to form the agent for altering the color of keratin fibers before application onto the fibers; and (2) leaving the agent on the keratin fibers for a period of time sufficient to achieve a desired change in the color of the fibers.

The method of the present disclosure is a method comprising applying the agent for altering the color of keratin fibers according to the present disclosure onto the keratin fibers. The agent for altering the color of the fibers is formed from combining the color base and oxidizing compositions of the present disclosure wherein the color is developed at alkaline pH and the oxidizing composition can be added at the moment of use or it can be used simultaneously with or sequentially to the color base composition.

Upon application and after a resting time on the keratin fibers, for example, ranging from about 1 to 60 minutes, such as from about 5 to 45 minutes, the keratin fibers are rinsed, optionally washed with shampoo and rinsed again, then dried.

The agent for altering the color of keratin fibers according to the disclosure can result from mixing at least the color base and oxidizing compositions of the present invention, including an oxidizing composition comprising at least one oxidizing agent as defined previously.

The oxidizing composition may be in the form of a powder, gel, liquid, foam, lotion, cream, mousse, and emulsion.

In one embodiment, the oxidizing composition is substantially anhydrous.

The term "substantially anhydrous" means that the oxidizing composition is either completely free of water or contains no appreciable amount of water, for example, no more than 5% by weight, or no more than 2% by weight, or no more than 1% by weight, based on the weight of the oxidizing composition. It should be noted that this refers for example to bound water, such as the water of crystallization of the salts or traces of water absorbed by the raw materials used in the preparation of the compositions according to the disclosure.

The oxidizing composition can contain at least one solvent, chosen from water, organic solvents, and mixtures thereof.

When the oxidizing composition is substantially anhydrous, the oxidizing composition may comprise at least one solvent chosen from organic solvents.

Suitable organic solvents for use in the oxidizing composition include ethanol, isopropyl alcohol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, glycerin, hydrocarbons such as straight chain hydrocarbons, mineral oil, polybutene, hydrogenated polyisobutene, hydrogenated polydecene, polydecene, squalane, petrolatum, isoparaffins, and mixtures, thereof.

The at least one solvent may, for example, be present in an amount ranging from about 0.5% to about 70% by weight, such as from about 2% to about 60% by weight, preferably from about 5 to about 50% by weight, relative to the total weight of the oxidizing composition.

The pH of the oxidizing composition can range from about 2 to about 12, such as from about 6 to about 11, and it may be adjusted to the desired value using acidifying/alkalizing agents that are well known in the art.

According to one embodiment of the invention, the agent for altering the color of keratin fibers is a composition comprising, in a cosmetically acceptable medium, at least one fatty substance having a viscosity greater than about 50 mm$^2$/s at 40° C., optionally, at least one additional fatty substance, at least one rheology modifying polymer selected from a crosslinked acrylate polymer in aqueous dispersion, at least one alkalizing agent, at least one short chain hydroxyl compound chosen from monoalcohols and polyols; at least one oxidative dye precursor; at least one oxidizing agent, and wherein the pH of the agent for altering the color of keratin fibers is from about 1 to about 7.

According to another embodiment of the invention, the agent for altering the color of keratin fibers can comprise two compositions, a color base composition in the form of a water-in-oil emulsion, containing, in a cosmetically acceptable medium, at least one fatty substance having a viscosity greater than about 50 mm$^2$/s at 40° C., optionally, at least one additional fatty substance, at least one rheology modifying polymer as defined previously, at least one alkalizing agent; and at least one short chain hydroxyl compound chosen from monoalcohols and polyols; and an oxidizing composition containing, in a cosmetically acceptable medium, at least one oxidizing agent, and wherein the pH of the agent for altering the color of keratin fibers is from about 1 to about 7.

According to yet another embodiment of the invention, the agent for altering the color of keratin fibers can result from mixing two units, including a first unit of a color base composition, containing, in a cosmetically acceptable medium, at least one fatty substance having a viscosity greater than about 50 mm$^2$/s at 40° C., optionally, at least one additional fatty substance, at least one rheology modifying polymer as defined previously, at least one alkalizing agent; and at least one short chain hydroxyl compound chosen from monoalcohols and polyols; and a second unit of an oxidizing composition containing, in a cosmetically acceptable medium, at least one oxidizing agent, and wherein the agent for altering the color of keratin fibers is from about 1 to about 7.

It has been surprisingly discovered that the combination of the fatty substance having a viscosity greater than about 50 mm$^2$/s at 40° C., and the rheology modifying polymer as defined previously results in a stable water-in-oil cream emulsion composition which, when combined with the oxidizing composition, produces a final mixture with a non-drip consistency that is still easy to spread on keratin fibers, such as hair.

It has also been discovered that the application of the agent for altering the color of keratin fibers onto the fibers results in satisfactory coloring of the fibers while utilizing lower amounts of the oxidizing agent compared to conventional oxidative dyeing compositions.

According to another embodiment of the invention, a kit for coloring keratin fibers is provided, comprising a first unit containing the above described color base composition and a second unit comprising the above described color base composition.

The coloring obtained using the compositions and method of the present disclosure may also be durable or wash/fade resistant.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The examples that follow serve to illustrate embodiments of the present disclosure without, however, being limiting in nature.

EXAMPLES

Example 1

Formulation Examples

TABLE 1

The following cream emulsion color base composition of the present disclosure was prepared:

| Ingredients (INCI Name) | formula A, % by weight pH <9.0 (pH > 7) |
|---|---|
| ETHANOLAMINE | 1 |
| ACRYLATES COPOLYMER (Carbopol ® Aqua SF-1) | 2.55 |
| EDTA | 0.2 |
| ALCOHOL DENAT. | 10 |
| SODIUM METABISULFITE | 0.5 |
| MINERAL OIL(high viscosity)* | 50 |
| ERYTHORBIC ACID | 0.3 |
| OXIDATIVE DYE PRECURSOR | 5% |
| WATER | Q.S. to 100 |

*viscosity from about 63 to about 70 mm$^2$/s at 40° C.; commercially available from the supplier Sonnenborn under the tradename Kaydol ® Heavy White Mineral Oil or from the supplier Exxonmobil Chemical under the tradename Primol ™ 352

The cream emulsion formula above was prepared as follow (1000 grams in total):

Acrylates Copolymer (commercially available as Carbopol® Aqua SF-1) was added to water and the resulting solution was mixed using a VMI Rayneri mixer equipped with a chopper blade. 10 g of Ethanolamine was added to neutralize the acrylates copolymer. The solution became a clear thick gel upon complete neutralization. The speed of mixing was increased to at least about 600 rpm. The solution became thicker & turned into a white paste. 80 g of mineral oil was added to the solution to create an emulsion and the speed of mixing was increased to at least about 1000 RPM. One half of the remainder of the oil (remainder of 420 grams), was then added to the emulsion and mixing was continued for about 10 minutes. The speed of mixing was increased to at least about 1200 RPM to ensure proper mixing. One half of the total concentration of alcohol denatured (ethanol) required was added to adjust or decrease the viscosity of the emulsion. The remainder of the mineral oil was then added and mixing was continued for a few minutes. If the additional fatty substance is employed, it can also be added at this stage, together with other additives that may be desired. The remainder of the alcohol denatured was also added. The antioxidants, sodium metabisulfite and erythorbic acid, were added to the emulsion. The speed of mixing was decreased. An acidifying or basifying agent was added to the emulsion to adjust the pH, if necessary.

It was found that even when high levels of mineral oil, e.g., 50% by weight, are incorporated into the formulas above, the formulas remained stable and in cream emulsion form.

TABLE 2

Oxidizing composition

| Phases | Ingredients (INCI Name) | % by weight |
|---|---|---|
| A | CETEARYL ALCOHOL | 6 |
| A | STEARETH-20 | 5 |
| A | MINERAL OIL(Low viscosity)* | 20 |
| A | PEG-4 RAPESEEDAMIDE | 1.2 |
| A | BHT | 0.0012 |
| A | TOCOPHEROL | 0.1 |
| B | WATER | 59.2 |
| B | GLYCERIN | 0.5 |
| B | PENTASODIUM PENTETATE | 0.06 |
| B | POLYQUATERNIUM-6 | 0.2 |
| B | HEXADIMETHRINE CHLORIDE | 0.15 |
| C | TETRASODIUM PYROPHOSPHATE | 0.03 |
| C | SODIUM STANNATE | 0.04 |
| D | PHOSPHORIC ACID | To adjust the pH |
| D | HYDROGEN PEROXIDE | 7.5 |
|  | Total | 100 |

*viscosity at about 30 mm²/s at 40° C.

The oxidizing composition above was prepared as follows:
Cetearyl Alcohol, Steareth-20, Mineral Oil, PEG-4 Rapeseedamide, and Tocopherol were added to a main beaker and heated to 80° C. (Phase A). Water was heated to 80° C. and added to phase A to form a solution. The solution was homogenized for 10 minutes at 2500 RPM. Glycerin, Pentasodium Pentetate, Polyquaterium-6, Hexadimethrine Chloride were then added to the solution and mixed for 10 minutes. Phase A was then cooled to 25° C. Hydrogen Peroxide was added to the solution and homogenized for 5 minutes. The homogenizer blade was removed and replaced with a chopper blade. Phosphoric Acid was added to adjust the pH to 2.0-2.40.

Example 2

Hair Coloration Studies; Colorimetric Measurements

The agent for altering the color of hair was prepared by mixing a liquid color base composition, pH 8.59 and an oxidizing composition and was used to color hair at the time of use in the following manner:

10 g of the dye base composition A was mixed with 10 g of the oxidizing composition B;
the resulting mixture resulting was applied onto hair swatches;
the hair swatches were then washed with shampoo, rinsed and then dried.

If desired, the color base composition can be mixed with the oxidizing composition in a 1:1 ratio, or a 1:2 ratio or a 1:3 ratio.

The resulting mixture has a pH below 7.

TABLE 3

Inventive cream emulsion color base compositions with different total amounts of dye

| INGREDIENTS (INCI Names) | Formula AA Inventive color base | Formula BB inventive color base |
|---|---|---|
| OXIDATIVE DYES/COUPLERS | 0.81 | 0.405 |
| ACRYLATES COPOLYMER (Carbopol ® Aqua SF-1) | 1.95 | 1.95 |
| ALCOHOL DENAT. | 10 | 10 |
| ASCORBIC ACID | — | — |
| FATTY ALCOHOLS, NONIONIC SURFACTANTS, FATTY ESTERS | — | — |
| CETYL HYDROXYETHYLCELLULOSE | — | — |
| EDTA | 0.2 | 0.2 |
| ERYTHORBIC ACID | 0.3 | 0.3 |
| ETHANOLAMINE | 1 | 1 |
| MINERAL OIL[a] | 50 | 50 |
| SODIUM METABISULFITE | 0.50 | 0.50 |
| THIOGLYCERIN | 0.004 | 0.002 |
| WATER | Q.S. 100 | Q.S. 100 |

[a]viscosity from about 63 to about 70 mm²/s at 40° C.; commercially available from the supplier Sonnenborn under the tradename Kaydol ® Heavy White Mineral Oil or from the supplier Exxonmobil Chemical under the tradename Primol ™ 352

Each of the formulas above was mixed with an oxidizing composition to form the agent for altering the color of hair (swatches). After dyeing the hair, the color of the swatches was measured with a Minolta CM2600d spectrocolorimeter (specular components included, 10 degrees angle, illuminant D65) in the CIEL*a*b* system. In this system, L* represents the intensity of the color, a* indicates the green/red color axis and b* the blue/yellow color axis.

According to this system, the greater the value of L, the lighter or less intense the color. Conversely, the lower the value of L, the darker or more intense the color.

DELTA E represents the change in color between a control hair swatch (undyed/untreated) and a treated (or dyed) hair swatch, and is determined from the change in L* values, a* values and b* values.

The colorimetric results obtained are given in the table below.

TABLE 4

| HAIR DYE TYPE[a] | Shade[b] | Formula #: | 90% Gray Hair Type | L* | CIE76 DE |
|---|---|---|---|---|---|
| Inventive color base | 6.54 | Formula AA | Unpermed | 23.12 | 4.12 |
| inventive color base | 6.54 | Formula BB | Unpermed | 22.75 | 3.52 |
| Inventive color base | 6.54 | Formula AA | Permed | 22.12 | 3.56 |
| inventive color base | 6.54 | Formula BB | Permed | 24.32 | 2.95 |

[a]formula plus oxidizing composition
[b]Shade 6.54 is a reddish purple shade
L* represents lightness or intensity of color; the higher the L value, the lighter the color of the hair.
**Delta-E (DE) represents the difference between two colors. If DE is less than 1.0 there is hardly any color difference that the human eye can perceive. If DE is greater than 1.0 there is a noticeable color difference by eye.

The mixture of the inventive color base compositions with an oxidizing composition according to the invention yielded a mixture with an alkaline pH. It was observed that the inventive compositions above deposited an intense red purple color onto the hair swatches. Moreover, the degree of color deposit and change in color as demonstrated by the L* and DE values on the hair treated with composition BB which had at least a 50% reduction in the amount of dye compounds were still comparable to the L* and DE values for the hair treated with composition AA. These results indicate that the amount of dyes can still be further reduced in the inventive compositions allowing for greater cost reduction and less stability/suspension problems with the dye compounds. The same results were observed for both unpermed and permed hair.

Example 3

Suspension/Stability Studies

| Ingredients | Formula (1) | Formula (2) | Formula (3) |
|---|---|---|---|
| Acrylates Copolymer (Carbopol ® Aqua SF-1) | 1.95 | 2.55 | 2.55 |
| Alcohol Denat. | 10 | 10 | 10 |
| Ascorbic Acid | — | — | — |
| Carbomer | — | — | — |
| Fatty Alcohol and surfactants | 5 | 5 | 5 |
| Disodium EDTA | — | — | — |
| EDTA | 0.2 | 0.2 | 0.2 |
| Erythorbic Acid | 0.3 | 0.3 | 0.3 |
| Ethanolamine | 4 | 4 | 4 |
| m-Aminophenol | — | — | — |
| Mineral Oil - (high viscosity)[a] | 50 | 50 | 50 |
| Sodium Cetearyl Sulfate | — | — | — |
| Sodium Metabisulfite | 0.5 | 0.5 | 0.5 |
| Sodium Sulfate | — | — | — |
| Sodium Sulfite | — | — | — |
| Water | Q.S. to 100 | Q.S. to 100 | Q.S. to 100 |

[a]viscosity from about 63 to about 70 mm$^2$/s at 40° C., commercially available from the supplier Sonneborn under the tradename Kaydol ® Heavy White Mineral Oil or from the supplier Exxonmobil Chemical under the tradename Primol ™ 352

The formulas above were heated from between 20° C.-60° C. Formulas (1) to (3) showed no phase separation and maintained their cream like structure, even in the presence of oxidation dyes and high levels of the mineral oil.

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

What is claimed is:

1. An agent for altering the color of keratin fibers comprising:
    (A) a color base composition, containing, in a cosmetically acceptable medium:
        (a) from about 50% to about 80% by weight of a fatty substance comprising:
            (i) at least 5% by weight of at least one fatty substance having a viscosity greater than about 50 mm$^2$/s at 40° C.; and
            (ii) from 0% to about 75% by weight of at least one additional fatty substance other than (A)(a)(i);
        all weights being based on the total weight of (A);
        (b) at least one rheology modifying polymer selected from a crosslinked acrylate polymer in aqueous dispersion;
        (c) at least one alkalizing agent;
        (d) at least one short alkyl chain hydroxy compound chosen from monoalcohols and polyols;
        (e) at least one oxidative dye precursor; and
    (B) an oxidizing composition comprising, in a cosmetically acceptable medium, at least one oxidizing agent; and
wherein the pH of the agent for altering the color of keratin fibers ranges from about 1 to about 7.

2. The agent according to claim 1, wherein (A)(a)(i) has a viscosity ranging from between greater than about 50 to about 100 mm$^2$/s at 40° C.

3. The agent according to claim 1, wherein (A)(a)(i) comprises mineral oil having a viscosity ranging from about 63 to about 70 mm$^2$/s at 40° C.

4. The agent according to claim 1, wherein (A)(a)(i) is present in an amount of from about 50% to about 70% by weight, based on the total weight of (A).

5. The agent according to claim 1, wherein (A)(a)(i) is present in an amount of from about 50% to about 60% by weight, based on the total weight of (A).

6. The agent according to claim 1, wherein (A)(a)(ii) is chosen from $C_6$-$C_{16}$ lower alkanes, non-silicone oils of mineral, plant, animal and synthetic origin, fatty alcohols, fatty acid esters, fatty alcohol esters, fatty acids, non-silicone waxes and silicones.

7. The agent according to claim 1, wherein (A)(b) is selected from crosslinked copolymers of acrylic or methacrylic acid and/or one or more of their C1-C6 alkyl esters.

8. The agent according to claim 1, wherein (A)(b) is selected from a crosslinked methacrylic acid/ethyl acrylate copolymer.

9. The agent according to claim 8, wherein (A)(b) is selected from acrylates copolymer in aqueous dispersion comprising about 30% by weight of total solids.

10. The agent according to claim 1, wherein (A)(b) is selected from a crosslinked anionic acrylate polymer.

11. The agent according to claim 10, wherein (A)(b) is selected from acrylates crosspolymer-4.

12. The agent according to claim 1, wherein (A)(b) is present in an amount of from about 0.3% to about 3% by weight, based on the total weight of (A).

13. The agent according to claim 1, wherein (A)(b) is present in an amount of from about 0.45% to about 2.75% by weight, based on the total weight of (A).

14. The agent according to claim 1, wherein (A)(b) is present in an amount of from about 0.5% to about 2% by weight, based on the total weight of (A).

15. The agent according to claim 1, wherein the weight ratio of (a) to (b) in (A) ranges from about 25:1 to about 3:1.

16. The agent according to claim 1, wherein the weight ratio of (a) to (b) in (A) ranges from about 15:1 to about 10:1.

17. The agent according to claim 1, wherein (A)(c) is chosen from alkali metal carbonates, alkali metal phosphate, organic amines, hydroxide base compounds, and derivatives thereof.

18. The agent according to claim 1, wherein (A)(c) is chosen from ethanolamine, triethanoloamine, 2-amino-2-methyl-1-propanol, and mixtures thereof.

19. The agent according to claim 1, wherein (A)(c) is present in an amount of from about 0.01% to about 30% by weight, based on the total weight of (A).

20. The agent according to claim 1, wherein (A)(c) is present in an amount of from about 0.5% to about 5% by weight, based on the total weight of (A).

21. The agent according to claim 1, wherein (A)(d) is chosen from ethanol, propanol, ethylene glycol, propylene glycol, butylene glycol, hexylene glycol, propane diol, and mixtures thereof.

22. The agent according to claim 1, wherein (A)(d) is present in an amount of from about 0.5% to about 15% by weight, based on the total weight of (A).

23. The agent according to claim 1, wherein (A)(d) is present in an amount of from about 5% to about 10% by weight, based on the total weight of (A).

24. The agent according to claim 1, wherein (A)(e) is chosen from oxidation bases and couplers, and mixtures thereof.

25. The agent according to claim 1, wherein (A)(e) is chosen from ortho- and para-phenylenediamine oxidation bases, double bases, ortho- and para-aminophenols, heterocyclic bases, as well as salts of addition of these compounds with an acid and meta-aminophenol, meta-phenylenediamine, meta-diphenol, naphthol couplers, heterocyclic couplers and acid salts thereof.

26. The agent according to claim 1, wherein (A) further comprises at least one direct dye.

27. The agent according to claim 1, wherein the pH of (A) ranges from greater than 7 to about 11.

28. The agent according to claim 1, wherein the pH of (A) ranges from about 7.5 to about 9.

29. The agent according to claim 1, wherein the at least one oxidizing agent is chosen from hydrogen peroxide, urea peroxide, alkali metal bromates, ferricyanides, peroxygenated salts, perborates, percarbonates, laccases, peroxidases, redox enzymes, and mixtures thereof.

30. The agent according to claim 1, wherein the at least one oxidizing agent is present in an amount of from about 0.05% to about 50% by weight, based on the total weight of (B).

31. The agent according to claim 1, wherein the at least one oxidizing agent is present in an amount of from about 1% to about 12% by weight, based on the total weight of (B).

32. The agent according to claim 1, wherein the pH of the agent ranges from about 2 to about 6.8.

33. The agent according to claim 1, wherein the pH of the agent ranges from about 4 to about 6.

34. The agent according to claim 1, wherein (A) further comprises at least one neutralizing agent chosen from ethylamines, ethyleneamines, alkanolamines, cyclic amines and other cyclic compounds, saturated or unsaturated, having one or more nitrogen atoms within the ring.

35. The agent according to claim 1, wherein (A) and/or (B) further comprises at least one auxiliary agent chosen from thickening agents and rheology modifying polymers other than (A)(b), cationic polymers, film forming polymers, pigments, dyes, humectants and moisturizing agents, emulsifying agents other than those that fall under the above-described fatty substances, structuring agents, propellants, surfactants, shine agents, and conditioning agents.

36. The agent according to claim 1, wherein (B) further comprises at least one fatty substance chosen from a fatty substance having a viscosity greater than about 50 mm$^2$/s at 40° C., an additional fatty substance other than the fatty substance having a viscosity greater than about 50 mm$^2$/s at 40° C., and mixtures thereof.

37. The agent according to claim 1, wherein the agent for altering the color of keratin fibers is substantially free of ammonia.

38. The agent according to claim 1, wherein the agent is a hair coloring ready-to-use composition.

39. A process for coloring keratin fibers, comprising:
(1) applying onto keratin fibers, an agent for altering the color of keratin fibers comprising:
(A) a color base composition, containing, in a cosmetically acceptable medium:
(a) from about 50% to about 80% by weight of a fatty substance comprising:
(i) at least 5% by weight of at least one fatty substance having a viscosity greater than about 50 mm$^2$/s at 40° C.; and
(ii) from 0% to about 75% by weight of at least one additional fatty substance other than (A)(a)(i);
all weights being based on the total weight of (A);
(b) at least one rheology modifying polymer selected from a crosslinked acrylate polymer in aqueous dispersion;
(c) at least one alkalizing agent;
(d) at least one short alkyl chain hydroxy compound chosen from monoalcohols and polyols;
(e) at least one oxidative dye precursor; and
(B) an oxidizing composition comprising, in a cosmetically acceptable medium, at least one oxidizing agent;
wherein (A) and (B) are mixed to form the agent for altering the color of keratin fibers before application onto the fibers; and
wherein the pH of the agent for altering the color of keratin fibers ranges from about 1 to about 7; and
(2) leaving the agent on the keratin fibers for a period of time sufficient to achieve a desired change in the color of the fibers.

40. A multi-compartment kit comprising:
(A) a first unit containing a color base composition, containing, in a cosmetically acceptable medium:
(a) from about 50% to about 80% by weight of a fatty substance comprising:
(i) at least 5% by weight of at least one fatty substance having a viscosity greater than about 50 mm$^2$/s at 40° C.; and
(ii) from 0% to about 75% by weight of at least one additional fatty substance other than (A)(a)(i);
all weights being based on the total weight of (A);
(b) at least one rheology modifying polymer selected from a crosslinked acrylate polymer in aqueous dispersion;
(c) at least one alkalizing agent;
(d) at least one short alkyl chain hydroxy compound chosen from monoalcohols and polyols; and
(e) at least one oxidative dye precursor;
wherein the pH of the color base composition ranges from about 7 to about 9; and
(B) a second unit containing an oxidizing composition comprising, in a cosmetically acceptable medium, at least one oxidizing agent.

41. An agent for altering the color of keratin fibers comprising, in a cosmetically acceptable medium:
(a) from about 50% to about 80% by weight of a fatty substance comprising:
(i) at least 5% by weight of at least one fatty substance having a viscosity greater than about 50 mm$^2$/s at 40° C.; and
(ii) from 0% to about 75% by weight of at least one additional fatty substance other than (a)(i);
all weights being based on the total weight of (A);
(b) from about 0.3% to about 3% by weight, based on the total weight of the agent, of at least one rheology modifying polymer selected from a crosslinked acrylate polymer in aqueous dispersion;
(c) at least one alkalizing agent;
(d) from about 0.5% to about 15% by weight, based on the total weight of the agent, of at least one short chain hydroxyl compound chosen from monoalcohols and polyols;
(e) at least one oxidative dye precursor; and
(f) at least one oxidizing agent; and
wherein the pH of the agent for altering the color of keratin fibers ranges from about 2 to about 6.5.

* * * * *